US011862328B2

(12) United States Patent
Gordon et al.

(10) Patent No.: US 11,862,328 B2
(45) Date of Patent: *Jan. 2, 2024

(54) JUGULAR VENOUS PRESSURE (JVP) MEASUREMENT

(71) Applicant: UnitedHealth Group Incorporated, Minnetonka, MN (US)

(72) Inventors: Marilyn L. Gordon, Cherry Hill, NJ (US); Gregory J. Boss, Saginaw, MI (US); Rama S. Ravindranathan, Edison, NJ (US); Jon Kevin Muse, Thompsons Station, TN (US); Guerino Bonetti, Berkeley Heights, NJ (US)

(73) Assignee: UnitedHealth Group Incorporated, Minnetonka, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/060,635

(22) Filed: Dec. 1, 2022

(65) Prior Publication Data

US 2023/0097815 A1     Mar. 30, 2023

Related U.S. Application Data

(63) Continuation of application No. 17/095,853, filed on Nov. 12, 2020, now Pat. No. 11,545,256.

(51) Int. Cl.
*G16H 30/40* (2018.01)
*G16H 30/20* (2018.01)
(Continued)

(52) U.S. Cl.
CPC ............ *G16H 30/40* (2018.01); *G06F 1/163* (2013.01); *G06N 20/00* (2019.01); *G16H 30/20* (2018.01); *G16H 50/20* (2018.01)

(58) Field of Classification Search
CPC ........ G16H 20/30; G16H 40/20; G16H 40/67; G16H 50/20; G16H 10/60; G16H 20/00;
(Continued)

(56) References Cited

U.S. PATENT DOCUMENTS 6,168,568 B1    1/2001  Gavriely
7,753,856 B2    7/2010  Dziubinski
(Continued)

FOREIGN PATENT DOCUMENTS

WO    2019/229543 A1    12/2019

OTHER PUBLICATIONS

U.S. Appl. No. 17/095,853, filed Nov. 12, 2020, 2002/0148713, Allowed.
(Continued)

*Primary Examiner* — Ajibola A Akinyemi
(74) *Attorney, Agent, or Firm* — ALSTON & BIRD LLP

(57) ABSTRACT

Embodiments of the invention provide apparatuses, systems, and methods for more accurate remote monitoring of a user's body. In some embodiments, a system for monitoring a user's body comprises a wearable device, a video sensor attached at a collar portion of the wearable device, a plurality of audio sensors spaced and attached at a body portion of a wearable device and a controller configured to determine a Jugular Venous Pressure (JVP) of the user, and determine audio characteristics of an output of the plurality of audio sensors to generate an audio heat map corresponding to at least one internal organ of the user.

20 Claims, 14 Drawing Sheets

(51) Int. Cl.
  *G06N 20/00* (2019.01)
  *G06F 1/16* (2006.01)
  *G16H 50/20* (2018.01)
(58) Field of Classification Search
  CPC ........ G16H 30/20; G16H 30/40; G16H 40/40;
             G16H 40/63; G16H 50/70; G16H 15/00;
             G16H 50/30; G16H 50/80; G16H 80/00;
             G16H 30/00
  USPC .......................................................... 382/128
  See application file for complete search history.

(56) References Cited

U.S. PATENT DOCUMENTS

| | | | |
|---|---|---|---|
| 8,506,480 | B2 | 8/2013 | Banet et al. |
| 9,125,564 | B2 | 9/2015 | Schmidt et al. |
| 9,521,956 | B2 | 12/2016 | Bedingham et al. |
| 9,750,429 | B1 | 9/2017 | Sackner et al. |
| 10,004,473 | B2 | 6/2018 | Tsai et al. |
| 10,055,549 | B2 | 8/2018 | Chung et al. |
| 10,080,528 | B2 | 9/2018 | DeBusschere et al. |
| 10,182,727 | B2 | 1/2019 | Gargiulo et al. |
| 10,217,218 | B2 | 2/2019 | Wu et al. |
| 10,398,364 | B2 | 9/2019 | Cheng |
| 10,595,813 | B2 | 3/2020 | Song et al. |
| 10,702,166 | B1 | 7/2020 | Freeman et al. |
| 10,709,414 | B1 | 7/2020 | McLane |
| 2007/0055151 | A1 | 3/2007 | Shertukde et al. |
| 2016/0036965 | A1* | 2/2016 | Kim ........................ H04M 1/67 455/411 |
| 2016/0086161 | A1* | 3/2016 | Zhou ................... G06F 3/04886 705/44 |
| 2016/0209636 | A1* | 7/2016 | Baleine .................. H04N 23/67 |
| 2017/0172459 | A1 | 6/2017 | Bernstein et al. |
| 2017/0209115 | A1 | 7/2017 | Lonnroth et al. |
| 2017/0325779 | A1 | 11/2017 | Spina et al. |
| 2018/0108440 | A1 | 4/2018 | Stevens et al. |
| 2018/0301221 | A1 | 10/2018 | Rothman |
| 2018/0325407 | A1 | 11/2018 | Varadan et al. |
| 2019/0014408 | A1 | 1/2019 | Tang |
| 2019/0083038 | A1 | 3/2019 | Griffin et al. |
| 2019/0142686 | A1 | 5/2019 | Lee |
| 2019/0192110 | A1 | 6/2019 | Parvaneh et al. |
| 2019/0216350 | A1 | 7/2019 | Sullivan et al. |
| 2019/0282178 | A1 | 9/2019 | Volosin et al. |
| 2019/0298269 | A1 | 10/2019 | Atashbar et al. |
| 2020/0008684 | A1 | 1/2020 | Feinberg |
| 2020/0060641 | A1 | 2/2020 | Shekhar et al. |
| 2020/0111578 | A1 | 4/2020 | Koblick et al. |
| 2021/0287004 | A1 | 9/2021 | Wexler et al. |
| 2021/0337307 | A1 | 10/2021 | Wexler et al. |
| 2022/0148713 | A1 | 5/2022 | Gordon et al. |
| 2022/0196678 | A1 | 6/2022 | Wilson et al. |

OTHER PUBLICATIONS

NonFinal Office Action for U.S. Appl. No. 17/096,035, dated Jan. 17, 2023, (7 pages), United States Patent and Trademark Office, US.
Abnousi, Freddy et al. "A Novel Noninvasive Method for Remote Heart Failure Monitoring: the EuleriAn video Magnification apPLications in heart Failure studY (AMPLIFY)," npj Digital Medicine, Aug. 21, 2019, vol. 2, No. 1, pp. 1-6. DOI: 10.1038/s41746-019-0159-0.
Gnitecki, January et al. "Separating Heart Sounds From Lung Sounds—Accurate Diagnosis of Respiratory Disease Depends on Understanding Noises," in IEEE Engineering in Medicine and Biology Magazine, Jan./Feb. 2007, pp. 20-29. Doi: 10.1109/MEMB.2007.289118.
Li, Shih-Hong et al. "Design of Wearable Breathing Sound Monitoring System for Real-Time Wheeze Detection," Sensor, (2017), vol. 17, No. 1, pp. 1-15. DOI: 10.3390/s17010171.
Marani, Roberto et al. "High Quality Heart and Lung Auscultation System for Diagnostic Use on Remote Patients in Real Time," The Open Biomedical Engineering Journal, (2010), vol. 4, pp. 250-256.
Michler, Fabian et al. "A Clinically Evaluated Interferometric Continuous-Wave Radar System for the Contactless Measurement of Human Vital Parameters," Sensors, (2019), vol. 11, No. 2492, pp. 1-19. DOI: 10.3390/s19112492.
Notice of Allowance for U.S. Appl. No. 17/095,853, dated Aug. 16, 2022, (15 pages), United States Patent and Trademark Office, US.
Pramono, Renard Xaviero Adhi et al. "Automatic Adventitious Respiratory Sound Analysis: A Systematic Review," PLos|One, vol. 12, No. 5:e0177296, May 26, 2017, pp. 1-43. DOI: 10.1371/journal.pone.0177926.
Notice of Allowance and Fee(s) Due for U.S. Appl. No. 17/096,035, dated Apr. 26, 2023, (7 pages), United States Patent and Trademark Office, US.

* cited by examiner

| 1302 | 1304 | 1304 | 1304 | 1304 | 1306 | 1306 | 1308 | 1310 | 1312 |
|---|---|---|---|---|---|---|---|---|---|
| MEMBER ID | Patient Demographic Notes | Pulse Ox | Heart Rate | Blood Pressure | Heart Sounds | Lung Sounds | JVP | Assessment | Action |
| 12345678 | 40 Year Old Male With Hypertension | 96% | 68 | 68 | Normal S1 At T Normal S2 At P, Regular Rhythm | Fine Crackles At Lung Base Sensors | 6cm | Stable | Continue Current Treatment Plan |
| 23456789 | 65 Year Old Female With Hypertension And Diabetes | 93% | 84 | 84 | Normal S1 At T Loud S2 At P, Regular Rhythm | Coarse Crackles Lung Base And Inferior Lobe Sensors | 8cm | Caution | Provider Office Called For Telehealth Visit; Take Your Prescribed Medication If You Have Not Done So Today |
| 34567890 | 70 Year Old Male With Coronary Artery Disease And Atrial Fibrilation | 88% | 124 | 124 | S3, S4 At M, Irregular Rhythm | Coarse Crackles And Wheezes Throughout Posterior And Anterior Sensors | 10cm | Emergent | 911 Called; Administer Oxygen If Available |

JUGULAR VENOUS PRESSURE (JVP) MEASUREMENT

CROSS REFERENCE TO RELATED APPLICATIONS

This application is a continuation of U.S. patent application Ser. No. 17/095,853 filed Nov. 12, 2020, the contents of which are incorporated by reference herein in their entireties.

BACKGROUND

Various embodiments of the present invention address technical challenges related to remote monitoring of a user's body. Through applied effort, ingenuity, and innovation, solutions to improve such apparatuses, systems, and methods have been realized in connection with embodiments of the present invention.

BRIEF SUMMARY

In general, embodiments of the present invention provide methods, apparatuses, systems, computing devices, computing entities, and/or the like for remote monitoring of characteristics a user's body.

In accordance with one aspect, a system is provided. The system comprises a wearable device defining a collar portion, a body portion, and an interior portion; a video sensor attached to the wearable device, wherein the video sensor is configured to capture video data within a field of view of the video sensor; a plurality of audio sensors spaced and attached to the wearable device, wherein each of the plurality of audio sensors is configured to capture audio data; and a controller configured to: determine a Jugular Venous Pressure (JVP) pressure of a user wearing the wearable device based at least in part on the video data captured by the video sensor; determine a JVP value corresponding with the pressure of the user; and determine characteristics of the audio data captured by the plurality of audio sensors to generate an audio heat map corresponding to an internal organ of the user.

In accordance with another aspect, a computer-implemented method is provided. The method comprises: receiving, by one or more processors, video data captured by a video sensor attached to a wearable device worn by the user, wherein the video sensor is configured to capture video data within a field of view of the video sensor; receiving, by the one or more processors, audio data captured by a plurality of audio sensors attached at a body portion of the wearable device; determining, by the one or more processors, a Jugular Venous Pressure (JVP) pressure value of the user based at least in part on the video data; determining, by the one or more processors, characteristics of the audio data to generate an audio heat map corresponding to an internal organ of the user; identifying, by the one or more processors, at least one of the plurality of audio sensors for collection of organ-specific data for the user; and storing, by the one or more processors, the pressure value and the organ-specific data for the user.

In accordance with yet another aspect, a computer program product is provided. The computer program product comprises at least one non-transitory computer-readable storage medium having computer-readable program code portions stored therein, the computer-readable program code portions configured to: receive video data captured by a video sensor attached to a wearable device worn by the user, wherein the video sensor is configured to capture video data within a field of view of the video sensor; receive audio data captured by a plurality of audio sensors attached at a body portion of the wearable device; determine a Jugular Venous Pressure (JVP) pressure value of the user based at least in part on the video data; determine characteristics of the audio data to generate an audio heat map corresponding to an internal organ of the user; identify at least one of the plurality of audio sensors for collection of organ-specific data for the user; and store the pressure value and the organ-specific data for the user.

BRIEF DESCRIPTION OF THE DRAWINGS

Figure 1:
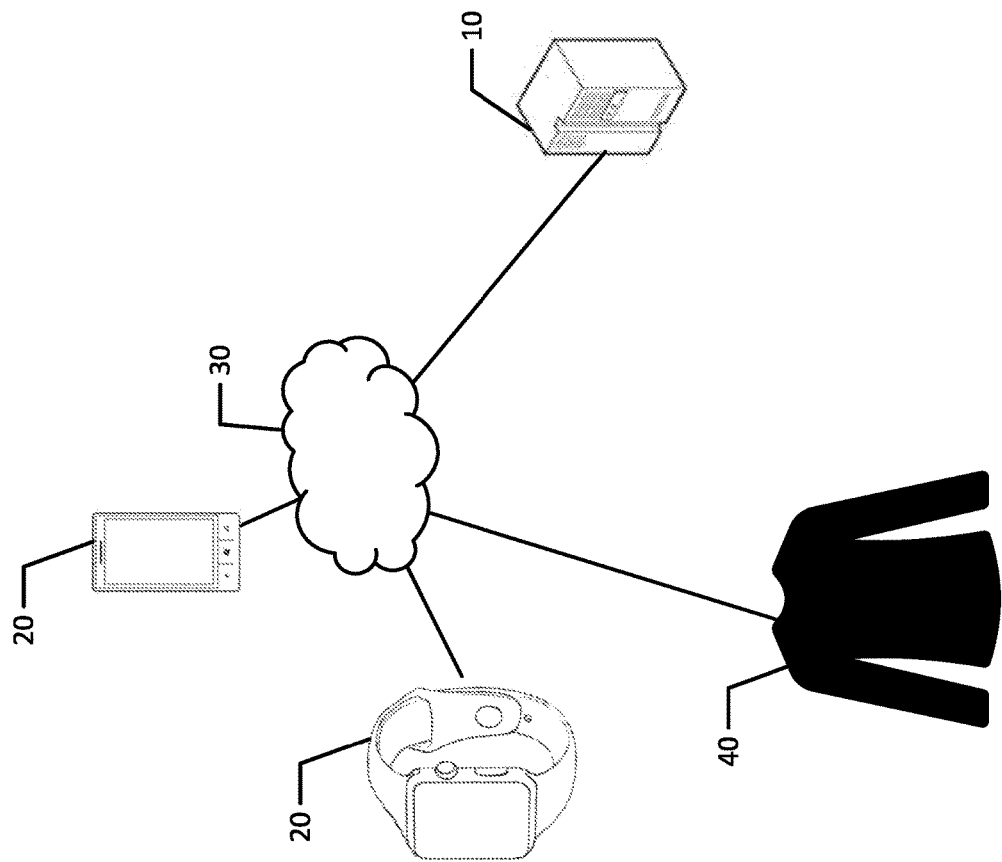
Figure 2:
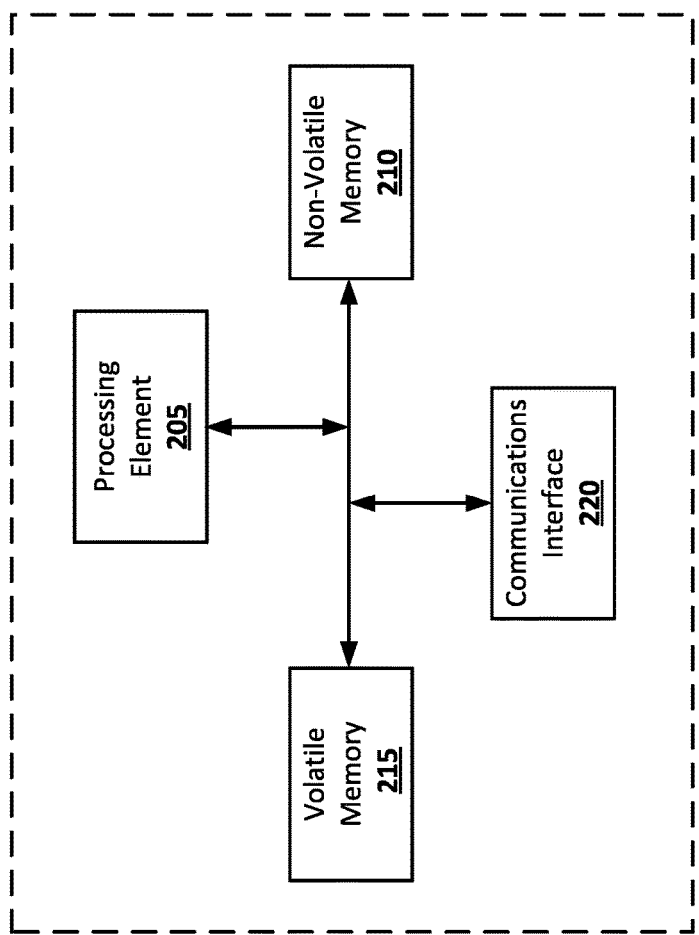
Figure 3:
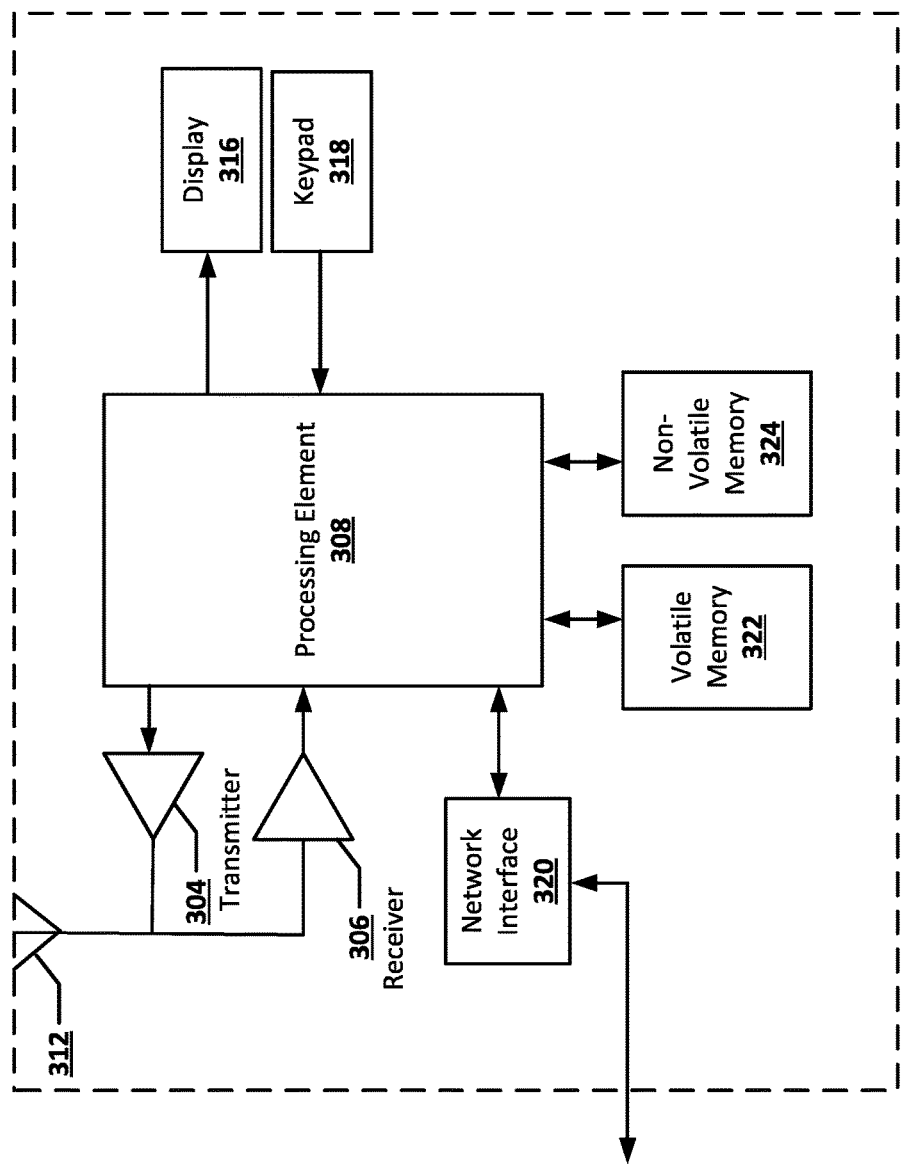
Figure 4:
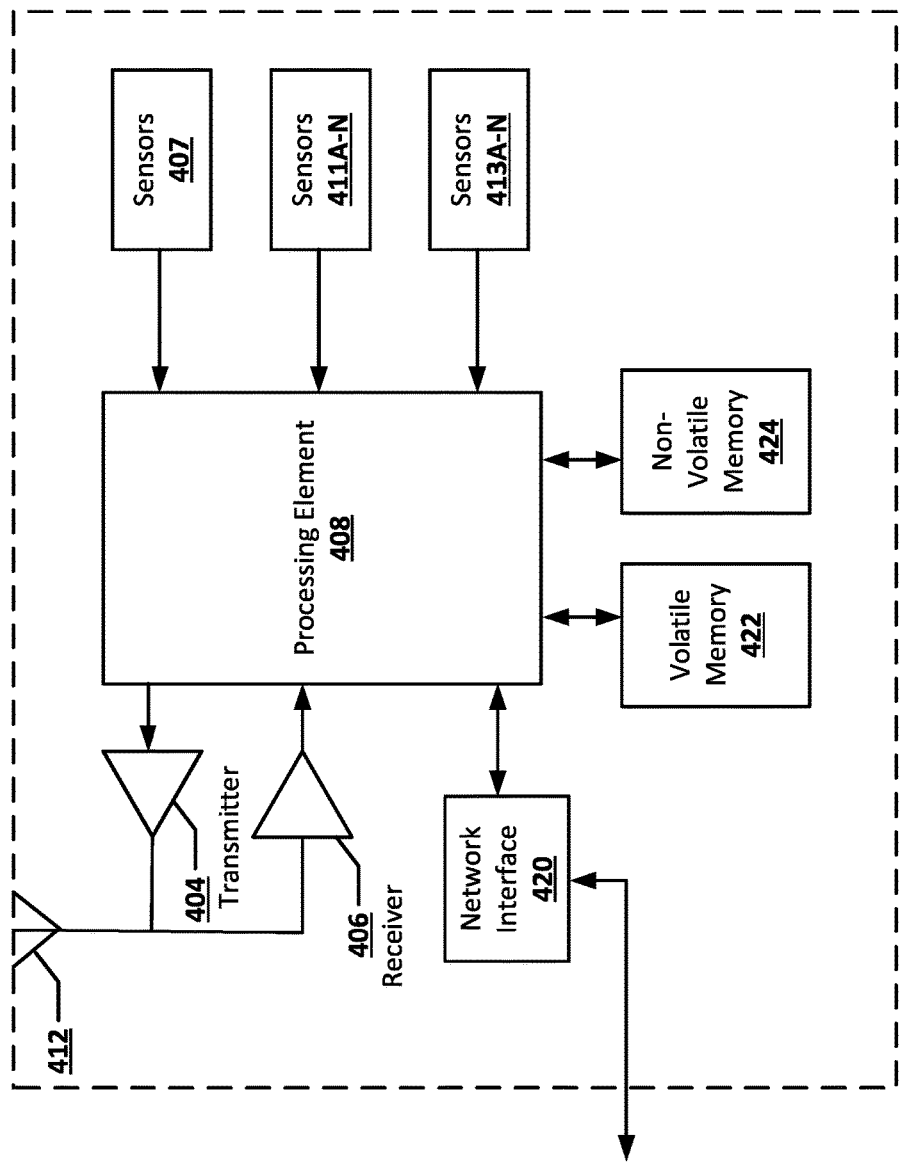
Figure 5:
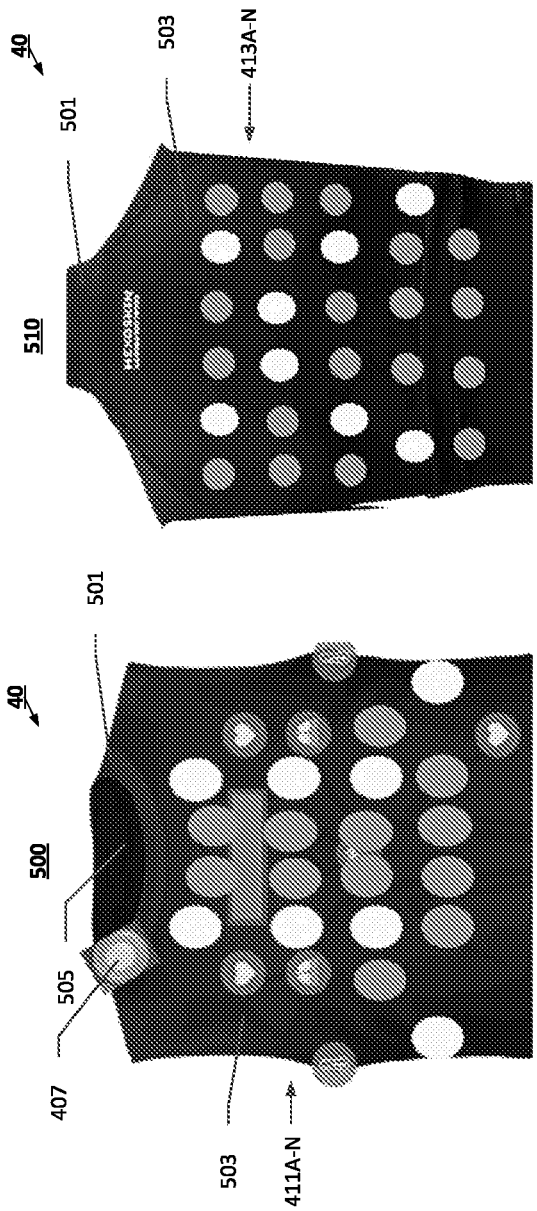
Figure 6:
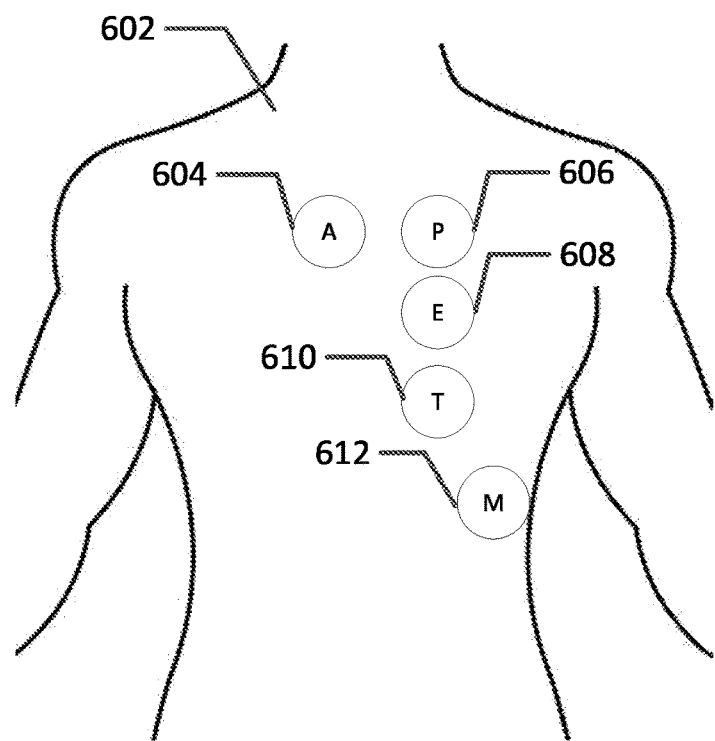
Figure 7A:
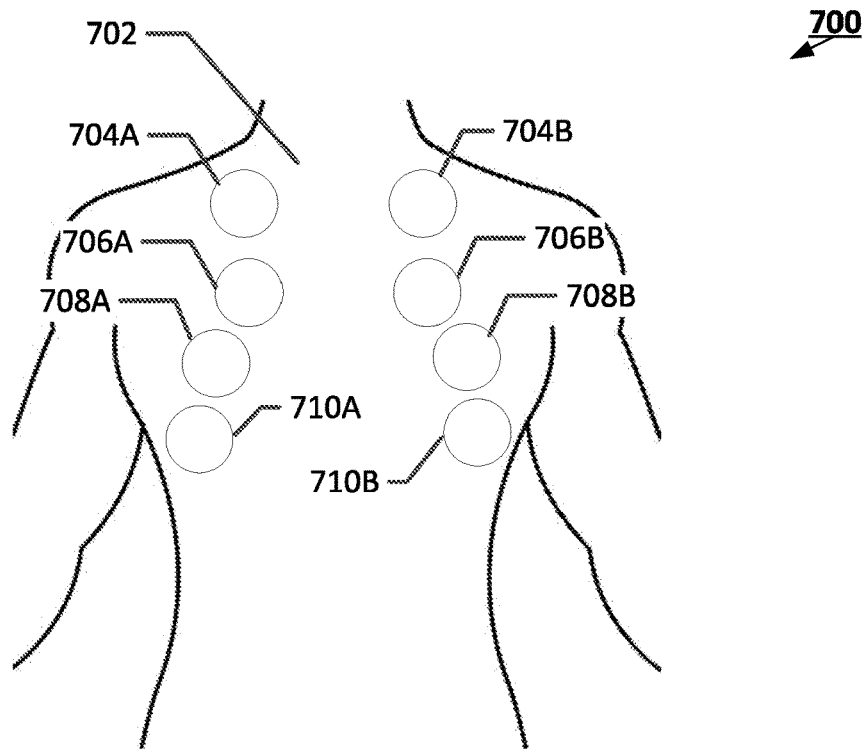
Figure 7B:
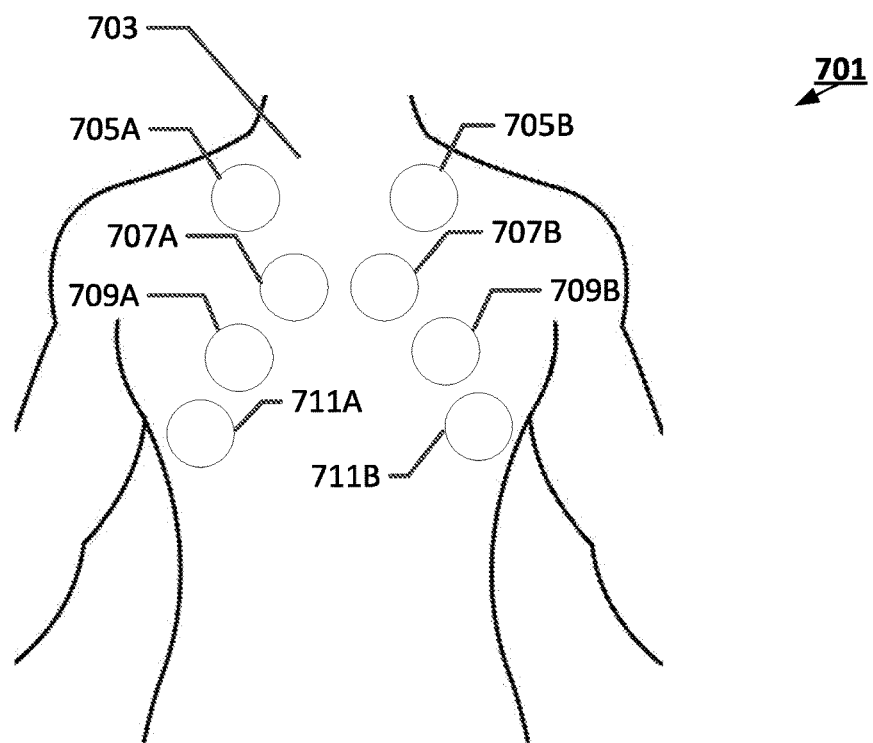
Figure 8:
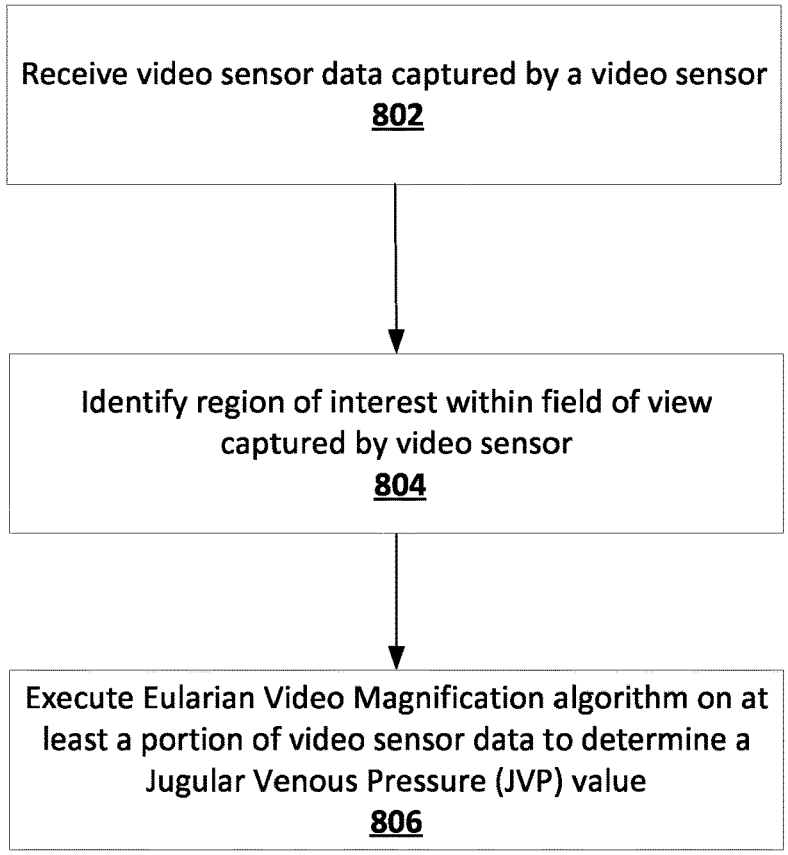
Figure 9:
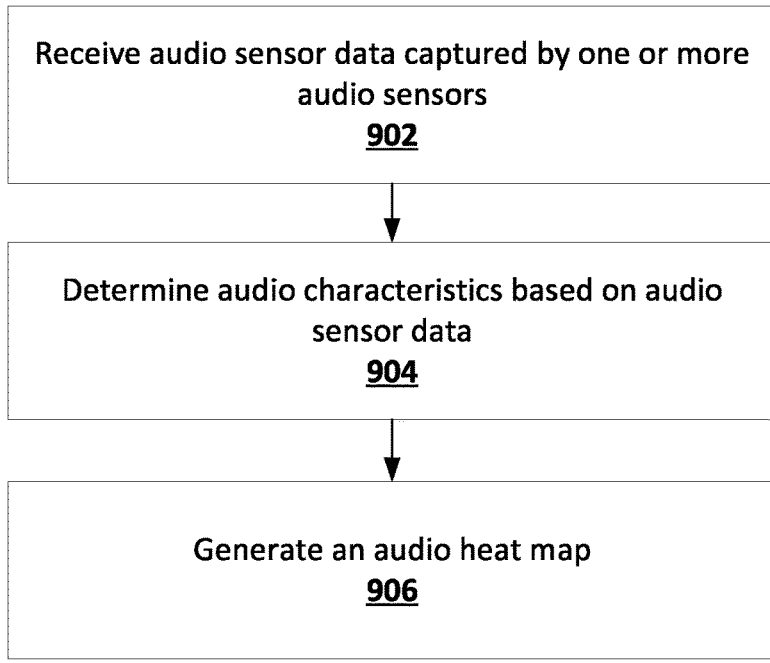
Figure 10:
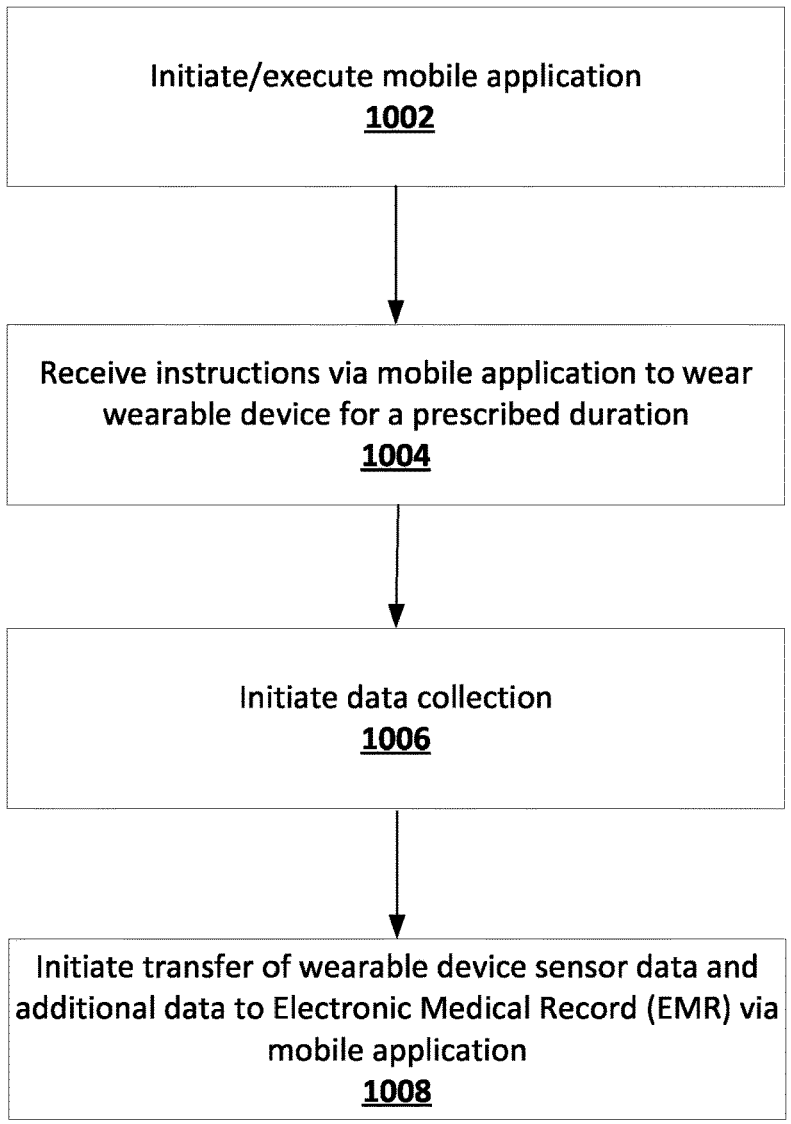
Figure 11:
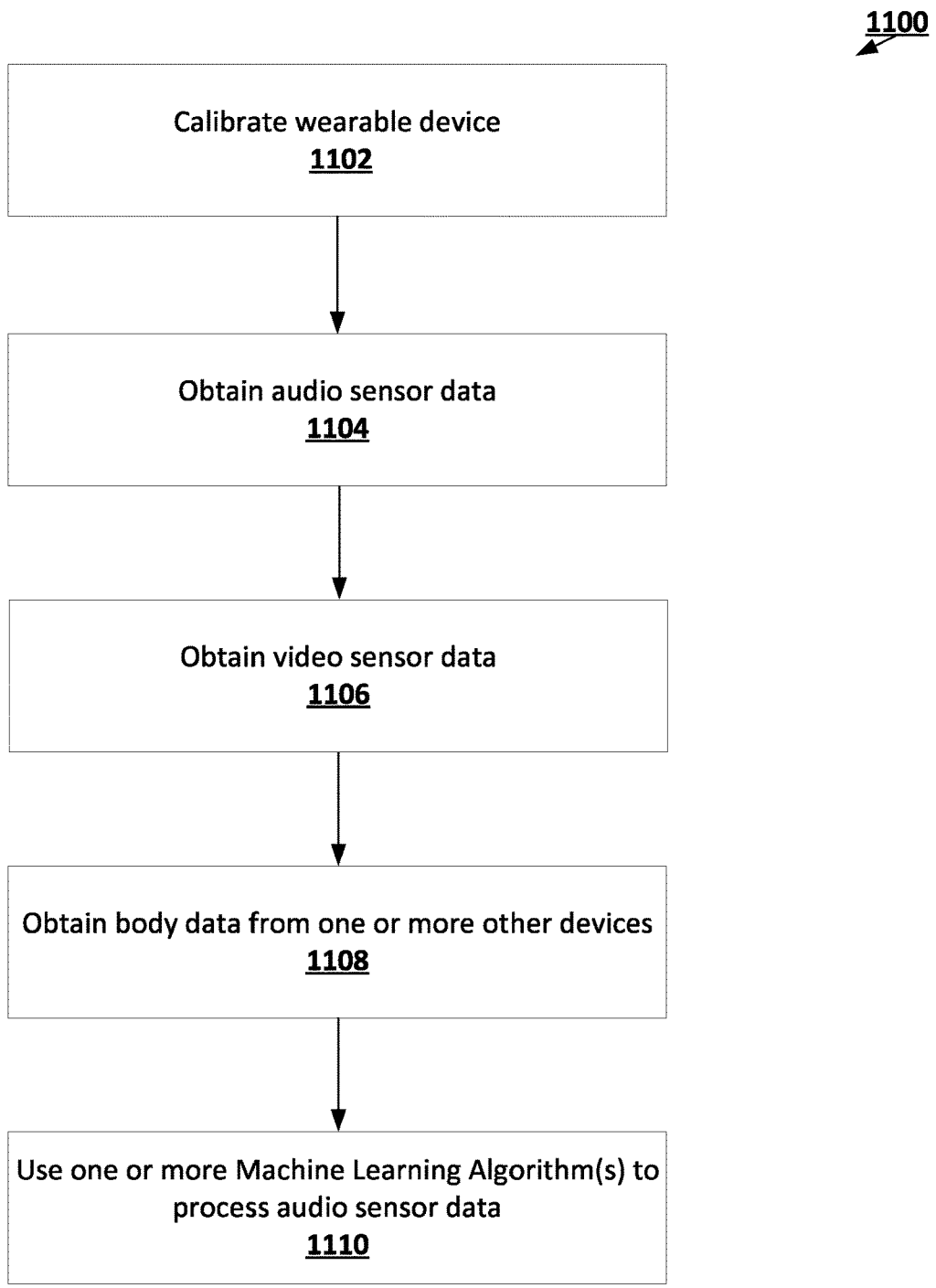
Figure 12:
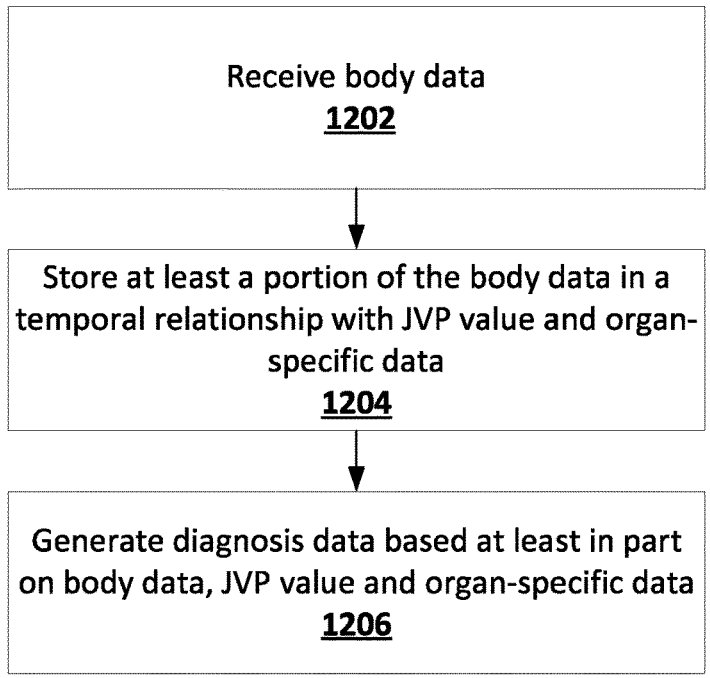
Figure 14:
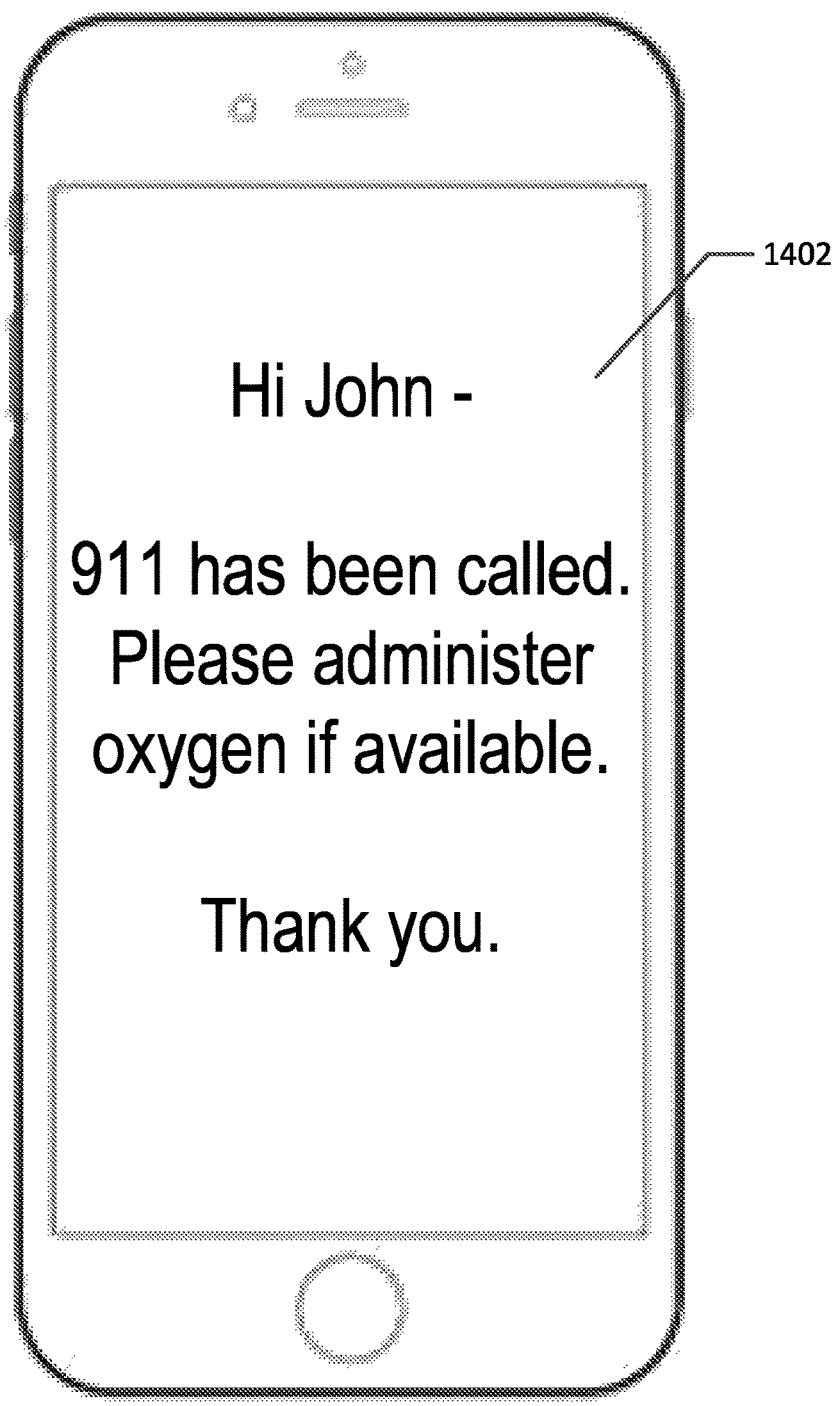

Having thus described the invention in general terms, reference will now be made to the accompanying drawings, which are not necessarily drawn to scale, and wherein:

FIG. 1 is an exemplary overview of a system architecture that can be used to practice various embodiments of the present invention;

FIG. 2 is an example schematic of a management computing entity in accordance with certain embodiments of the present invention;

FIG. 3 is an example schematic of a user computing entity in accordance with certain embodiments of the present invention;

FIG. 4 is an example schematic of a wearable device in accordance with certain embodiments of the present invention;

FIGS. 5A and 5B are exemplary views of a wearable device, in accordance with certain embodiments of the present invention;

FIG. 6 is an example schematic illustrating heart regions associated with an anterior portion of a body, in accordance with certain embodiments of the present invention;

FIGS. 7A and 7B are example schematics illustrating lung regions associated with an anterior and posterior portion of a body, in accordance with certain embodiments of the present invention;

FIG. 8 is a flowchart diagram illustrating an example process for determining a Jugular Venous Pressure (JVP) value, in accordance with certain embodiments of the present invention;

FIG. 9 is a flowchart diagram illustrating an example process for generating an audio heat map, in accordance with certain embodiments of the present invention;

FIG. 10 is a flowchart diagram illustrating an example setup process, in accordance with certain embodiments of the present invention;

FIG. 11 is a flowchart diagram illustrating an example clinical procedure process, in accordance with certain embodiments of the present invention;

FIG. 12 is a flowchart diagram illustrating an example process for generating diagnosis data, in accordance with certain embodiments of the present invention;

FIG. 13 provides an example view of a user interface, in accordance with certain embodiments of the present invention; and FIG. 14 provides another example view of a user interface, in accordance with certain embodiments of the present invention.

DETAILED DESCRIPTION

Various embodiments of the present invention now will be described more fully hereinafter with reference to the accompanying drawings, in which some, but not all embodiments are shown. Indeed, various configurations as discussed herein may be embodied in many different forms and should not be construed as limited to the embodiments set forth herein; rather, these embodiments are provided so that this disclosure will satisfy applicable legal requirements. The term "or" (also designated as "/") is used herein in both the alternative and conjunctive sense, unless otherwise indicated. The terms "illustrative" and "exemplary" are used to be examples with no indication of quality level. Like numbers refer to like elements throughout.

I. Overview

Various embodiments are directed to techniques, systems, apparatuses and/or the like for remote monitoring of characteristics of a user's body. There is a need for remote monitoring and accurate prognoses for vulnerable patients at risk for heart failure decompensation and other health conditions having significant morbidity levels to provide a more detailed and complete view of the patient's bodily function even when the patient is outside clinical settings. Existing systems and techniques for remote monitoring of a user's body are not configured for and/or optimized for remotely monitoring users in real-time, generating a diagnosis, and determining one or more actions to take in relation to a user. For example, existing systems may be incapable of detecting an emergency or urgent condition of the user to enable appropriate corrective actions, such as calling emergency services, directing the user to take medication or specific actions and/or the like.

Many health monitoring devices are inadequate for remote monitoring applications. Additionally, existing wearable devices are difficult to configure for remote use and often require extensive customization in order to fit the body of particular users. For example, sensors must be properly aligned for specific organs, thereby increasing operational complexity and diminishing the value and practicality of such systems outside clinical settings.

There is a need for improved systems and techniques for providing remote monitoring of users' body characteristics that facilitates accurate and timely diagnoses of potential emergency and/or urgent conditions of the user and to facilitate execution of one or more responsive automated actions in response to any detected emergency and/or urgent conditions of a user. There is also a need for devices that do not need to be custom-fit that can be easily calibrated and configured for a particular user in order to obtain useful information and to generate accurate diagnoses.

Various embodiments of the present invention utilize sensor arrays within a wearable device and dynamic sensor selection (e.g., by a controller associated with the wearable device) to obtain information. The obtained information, in combination with models (e.g., machine learning models/algorithms, a Eulerian Video Magnification algorithm and/or the like) and additional data obtained from other sources can be used to generate accurate diagnostic data for a user. Using the methods described herein leads to more accurate and timely predictions which can also be used to generate user interface data and to determine one or more actions to take in relation to a detected urgent or emergency condition associated with the user. In doing so, various embodiments of the present invention make substantial technical contributions to the field of remote monitoring and substantially improve state-of-the-art systems.

II. Definitions of Certain Terms

The term "body" may refer to a user's physical body, and the term may specifically be utilized to refer to a portion of a user's body, including at least a portion of one or more internal/external organs of a user. In general, the terms user, patient, wearer, individual, person and/or similar words are used herein interchangeably. Organs include, for example without limitation, the lungs, the heart, the kidneys, the bladder, the stomach, the intestines, the skin and the brain.

The term "wearable device" may refer to an article or garment configured to fit closely to a user's body. The wearable device may be or comprise, for example without limitation, a jacket, vest, shirt, pants, shorts, underwear, hat, socks, scarf, neck warmer, leg gaiter, head band, arm band, leg band, and/or the like. The wearable device may comprise at least a controller/processor, a wireless communication transceiver and various sensors (e.g., video sensors, audio sensors and/or the like).

The term "video sensor" may refer to a camera and/or image capturing device configured to capture image data/information.

The term "audio sensor" may refer to a microphone and/or sound capturing device configured to capture audio data/information (e.g., audio sensor data). Audio sensors may be configured to communicate captured audio data/information to a controller as discussed herein, and such communication may proceed wirelessly (e.g., via Bluetooth or other wireless communication protocol) or via wired communication.

The term "audio characteristics" may refer to various attributes of audio sensor data such as clarity/quality, pitch, loudness, duration, intensity, frequency, and timbre.

The term "Eulerian Video Magnification (EVM) algorithm" may refer to a spatio-temporal video processing algorithm that processes an input video sequence comprising a plurality of frames by applying spatial decomposition and temporal filtering in order to reconstruct the plurality of frames. The resulting signal is then amplified, facilitating visualization of otherwise imperceptible/minute changes in motion captured in the frames. The video sequence output of the EVM algorithm reveals features at selected temporal frequencies that are imperceptible in the unprocessed input video sequence.

The term "Jugular Venous Pressure (JVP)" may refer to an indirectly observed pressure for the venous system of a user's body that is typically measured through visualization of pulsations of the internal jugular vein. In order to measure a user's JVP in a clinical setting, a patient (specifically the patient's torso) is usually positioned at a 45° degree incline and pulsations of the internal jugular vein are visualized, typically by observing the right hand side of a patient's neck when the head is turned slightly to the left. The height of the observed pulsations with reference to the patient's sternal angle corresponds with the patient's central venous pressure. A JVP measurement/value for a healthy patient should be within a threshold height (e.g., between about 3 and 4 cm) when measured vertically from the patient's sternal angle to the highest point of pulsation corresponding with the right internal jugular vein.

The term "audio heat map" may refer to a visual representation (e.g., spectrogram, sonograph, voiceprint and/or the like) of the spectrum of frequencies of a signal (e.g., audio data) as it varies with time and location. The audio heat map may be an image illustrating various intensities of the represented data (e.g., audio data) using variations of color and/or brightness in a two-dimensional graphic that enables a user to correlate the location of a particular color/brightness (representative of an intensity of some audio characteristic) with a location of generation of the audio characteristic on the patient's body and/or within the sensor array of the wearable device.

The term "body data" may refer to physiological information/data, biometric information/data, accelerometer information/data, location information/data, time information/data and/or the like. Body data may be collected and/or generated by one or more sensors associated with the patient, such as sensors within a mobile device, sensors within a wearable device, sensors associated with one or more devices commonly used by the user (e.g., a glucose monitoring device), a weather station located near the user (e.g., as determined by location data associated with the user), and/or the like. In certain embodiments, the body data may include heart rate data, oxygen saturation data, pulse rate data, body temperature data, breath rate data, perspiration data, blink rate data, blood pressure data, neural activity data, cardiovascular data, pulmonary data, and/or various other types of information/data. In some embodiments, the body data may comprise environmental data corresponding with a location of a user such as air quality and air temperature data, allergen data, pollen count, weather information/data, water contamination data, and/or the like.

The term "machine learning model/algorithm" may refer to computer-implemented operations and/or parameters which are configured to perform predictive tasks. The machine learning model/algorithm may be trained on historical data. By way of example, the machine learning model/algorithm may be a neural network, a convolutional neural network (CNN), a recurrent neural network (RNN), and/or the like.

III. Computer Program Products, Methods, and Computing Devices

Embodiments of the present invention may be implemented in various ways, including as computer program products that comprise articles of manufacture. Such computer program products may include one or more software components including, for example, software objects, methods, data structures, and/or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatus, systems, computing devices, computing entities, and/or the like. As such, embodiments of the present invention may take the form of a data structure, apparatus, system, computing device, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises combination of computer program products and hardware performing certain steps or operations.

Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

IV. Exemplary System Architecture

FIG. 1 provides an example system architecture 100 that can be used in conjunction with various embodiments of the present invention. As shown in FIG. 1, the system architecture 100 may comprise one or more management computing entities 10, one or more user computing entities 20, one or more networks 30, one or more wearable devices 40 and/or the like. Each of the components of the system may be in electronic communication with, for example, one another over the same or different wireless or wired networks 30 including, for example, a wired or wireless Personal Area Network (PAN), Local Area Network (LAN), Metropolitan Area Network (MAN), Wide Area Network (WAN), and/or the like. Additionally, while FIG. 1 illustrates certain system devices as separate, standalone devices, the various embodiments are not limited to this particular architecture.

Exemplary Management Computing Entity

FIG. 2 provides a schematic of a management computing entity 10 according to one embodiment of the present invention. In general, the terms computing device, entity, device, system, and/or similar words used herein interchangeably may refer to, for example, one or more computers, computing devices, computing entities, desktop computers, mobile phones, tablets, phablets, notebooks, laptops, distributed systems, terminals, servers or server networks, blades, gateways, switches, processing devices, set-top boxes, relays, routers, network access points, base stations, the like, and/or any combination of devices adapted to perform the functions, operations, and/or processes described herein. Such functions, operations, and/or processes may include, for example, transmitting, receiving, operating on, processing, displaying, storing, determining, generating/creating, monitoring, evaluating, comparing, and/or similar terms used herein interchangeably. In one embodiment, these functions, operations, and/or processes can be performed on data, content, information, and/or similar terms used herein interchangeably.

As indicated, in one embodiment, the management computing entity 10 may also include one or more network and/or communications interfaces 220 for communicating with various computing entities, such as by communicating data, content, information, and/or similar terms used herein interchangeably that can be transmitted, received, operated on, processed, displayed, stored, and/or the like.

As shown in FIG. 2, in one embodiment, the management computing entity 10 may include or be in communication with one or more processing elements 205 (also referred to as processors, processing circuitry, and/or similar terms used herein interchangeably) that communicate with other elements within the management computing entity 10 via a bus, for example. As will be understood, the processing element 205 may be embodied in a number of different ways. For example, the processing element 205 may be embodied as one or more complex programmable logic devices (CPLDs), microprocessors, multi-core processors, coprocessing devices, application-specific instruction-set processors (ASIPs), and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like. As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present invention when configured accordingly.

In one embodiment, the management computing entity 10 may further include or be in communication with non-volatile media (also referred to as non-volatile storage, memory, memory storage, memory circuitry and/or similar terms used herein interchangeably). In one embodiment, the non-volatile storage or memory may include one or more non-volatile storage or memory media 210 as described above, such as hard disks, ROM, PROM, EPROM, EEPROM, flash memory, MMCs, SD memory cards, Memory Sticks, CBRAM, PRAM, FeRAM, RRAM, SONOS, racetrack memory, and/or the like. As will be recognized, the non-volatile storage or memory media may store databases, database instances, database management system entities, data, applications, programs, program modules, scripts, source code, object code, byte code, compiled code, interpreted code, machine code, executable instructions, and/or the like. The term database, database instance, database management system entity, and/or similar terms used herein interchangeably may refer to a structured collection of records or information/data that is stored in a computer-readable storage medium, such as via a relational database, hierarchical database, and/or network database.

In one embodiment, the management computing entity 10 may further include or be in communication with volatile media (also referred to as volatile storage, memory, memory storage, memory circuitry and/or similar terms used herein interchangeably). In one embodiment, the volatile storage or memory may also include one or more volatile storage or memory media 215 as described above, such as RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. As will be recognized, the volatile storage or memory media may be used to store at least portions of the databases, database instances, database management system entities, data, applications, programs, program modules, scripts, source code, object code, byte code, compiled code, interpreted code, machine code, executable instructions, and/or the like being executed by, for example, the processing element 205. Thus, the databases, database instances, database management system entities, data, applications, programs, program modules, scripts, source code, object code, byte code, compiled code, interpreted code, machine code, executable instructions, and/or the like may be used to control certain aspects of the operation of the management computing entity 10 with the assistance of the processing element 205 and the operating system.

As indicated, in one embodiment, the management computing entity 10 may also include one or more network and/or communications interfaces 220 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, management computing entity 10 may be configured to communicate via wireless external communication networks using any of a variety of protocols, such as general packet radio service (GPRS), Universal Mobile Telecommunications System (UMTS), Code Division Multiple Access 200 (CDMA200), CDMA200 1×(1× RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), IR protocols, NFC protocols, RFID protocols, IR protocols, ZigBee protocols, Z-Wave protocols, 6LoWPAN protocols, Wibree, Bluetooth protocols, wireless universal serial bus (USB) protocols, and/or any other wireless protocol. The management computing entity 10 may use such protocols and standards to communicate using Border Gateway Protocol (BGP), Dynamic Host Configuration Protocol (DHCP), Domain Name System (DNS), File Transfer Protocol (FTP), Hypertext Transfer Protocol (HTTP), HTTP over TLS/SSL/Secure, Internet Message Access Protocol (IMAP), Network Time Protocol (NTP), Simple Mail Transfer Protocol (SMTP), Telnet, Transport Layer Security (TLS), Secure Sockets Layer (SSL), Internet Protocol (IP), Transmission Control Protocol (TCP), User Datagram Protocol (UDP), Datagram Congestion Control Protocol (DCCP), Stream Control Transmission Protocol (SCTP), HyperText Markup Language (HTML), and/or the like.

As will be appreciated, one or more of the management computing entity's components may be located remotely from other management computing entity 10 components, such as in a distributed system. Furthermore, one or more of the components may be aggregated and additional components performing functions described herein may be included in the management computing entity 10. Thus, the management computing entity 10 can be adapted to accommodate a variety of needs and circumstances, such as including various components described with regard to a mobile application executing on the user computing entity 20, including various input/output interfaces.

Exemplary User Computing Entity

FIG. 3 provides an illustrative schematic representative of user computing entity 20 that can be used in conjunction with embodiments of the present invention. In various embodiments, the user computing entity 20 may be or comprise one or more mobile devices, wearable computing devices, and/or the like.

As shown in FIG. 3, a user computing entity 20 can include an antenna 312, a transmitter 304 (e.g., radio), a receiver 306 (e.g., radio), and a processing element 308 that provides signals to and receives signals from the transmitter 304 and receiver 306, respectively. The signals provided to and received from the transmitter 304 and the receiver 306, respectively, may include signaling information/data in accordance with an air interface standard of applicable wireless systems to communicate with various devices, such as a management computing entity 10, another user computing entity 20, and/or the like. In an example embodiment, the transmitter 304 and/or receiver 306 are configured to communicate via one or more SRC protocols. For example, the transmitter 304 and/or receiver 306 may be configured to transmit and/or receive information/data, transmissions, and/or the like of at least one of Bluetooth protocols, low energy Bluetooth protocols, NFC protocols, RFID protocols, IR protocols, Wi-Fi protocols, ZigBee protocols, Z-Wave protocols, 6LoWPAN protocols, and/or other short range communication protocol. In various embodiments, the antenna 312, transmitter 304, and receiver 306 may be configured to communicate via one or more long range protocols, such as GPRS, UMTS, CDMA200, 1×RTT, WCDMA, GSM, EDGE, TD-SCDMA, LTE, E-UTRAN, EVDO, HSPA, HSDPA, Wi-Fi, Wi-Fi Direct, WiMAX, and/or the like. The user computing entity 20 may also include one or more network and/or communications interfaces 320 for communicating with various computing entities, such as by communicating data, content, information, and/or similar terms used herein interchangeably that can be transmitted, received, operated on, processed, displayed, stored, and/or the like.

In this regard, the user computing entity 20 may be capable of operating with one or more air interface standards, communication protocols, modulation types, and access types. More particularly, the user computing entity 20 may operate in accordance with any of a number of wireless communication standards and protocols. In a particular embodiment, the user computing entity 20 may operate in accordance with multiple wireless communication standards and protocols, such as GPRS, UMTS, CDMA200, 1×RTT, WCDMA, TD-SCDMA, LTE, E-UTRAN, EVDO, HSPA, HSDPA, Wi-Fi, WiMAX, UWB, IR protocols, Bluetooth protocols, USB protocols, and/or any other wireless protocol.

Via these communication standards and protocols, the user computing entity 20 can communicate with various other devices using concepts such as Unstructured Supplementary Service information/data (USSD), Short Message Service (SMS), Multimedia Messaging Service (MMS), Dual-Tone Multi-Frequency Signaling (DTMF), and/or Subscriber Identity Module Dialer (SIM dialer). The user computing entity 20 can also download changes, add-ons, and updates, for instance, to its firmware, software (e.g., including executable instructions, applications, program modules), and operating system.

According to one embodiment, the user computing entity 20 may include location determining aspects, devices, modules, functionalities, and/or similar words used herein interchangeably to acquire location information/data regularly, continuously, or in response to certain triggers. For example, the user computing entity 20 may include outdoor positioning aspects, such as a location module adapted to acquire, for example, latitude, longitude, altitude, geocode, course, direction, heading, speed, UTC, date, and/or various other information/data. In one embodiment, the location module can acquire information/data, sometimes known as ephemeris information/data, by identifying the number of satellites in view and the relative positions of those satellites. The satellites may be a variety of different satellites, including LEO satellite systems, DOD satellite systems, the European Union Galileo positioning systems, the Chinese Compass navigation systems, Indian Regional Navigational satellite systems, and/or the like. Alternatively, the location information/data may be determined by triangulating the apparatus's 30 position in connection with a variety of other systems, including cellular towers, Wi-Fi access points, and/or the like. Similarly, the user computing entity 20 may include indoor positioning aspects, such as a location module adapted to acquire, for example, latitude, longitude, altitude, geocode, course, direction, heading, speed, time, date, and/or various other information/data. Some of the indoor aspects may use various position or location technologies including RFID tags, indoor beacons or transmitters, Wi-Fi access points, cellular towers, nearby computing entities (e.g., smartphones, laptops) and/or the like. For instance, such technologies may include iBeacons, Gimbal proximity beacons, BLE transmitters, NFC transmitters, and/or the like. These indoor positioning aspects can be used in a variety of settings to determine the location of someone or something to within inches or centimeters.

The user computing entity 20 may also comprise a user interface device comprising one or more user input/output interfaces (e.g., a display 316 and/or speaker/speaker driver coupled to a processing element 308 and a touch interface, keyboard, mouse, and/or microphone coupled to a processing element 308). For example, the user interface may be configured to provide a mobile application, browser, interactive user interface, dashboard, webpage, and/or similar words used herein interchangeably executing on and/or accessible via the user computing entity 20 to cause display or audible presentation of information/data and for user interaction therewith via one or more user input interfaces. Moreover, the user interface can comprise or be in communication with any of a number of devices allowing the user computing entity 20 to receive information/data, such as a keypad 318 (hard or soft), a touch display, voice/speech or motion interfaces, scanners, readers, or other input device. In embodiments including a keypad 318, the keypad 318 can include (or cause display of) the conventional numeric (0-9) and related keys (#, *), and other keys used for operating the user computing entity 20 and may include a full set of alphabetic keys or set of keys that may be activated to provide a full set of alphanumeric keys. In addition to providing input, the user input interface can be used, for example, to activate or deactivate certain functions, such as screen savers and/or sleep modes. Through such inputs the user computing entity 20 can capture, collect, store information/data, user interaction/input, and/or the like.

The user computing entity 20 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, RRAM, SONOS, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. The volatile and non-volatile storage or memory can store databases, database instances, database management system entities, information/data, applications, programs, program modules, scripts, source code, object code, byte code, compiled code, interpreted code, machine code, executable instructions, and/or the like to implement the functions of the user computing entity 20.

Exemplary Wearable Device Controller

The wearable device 40 may comprise or be an article or garment configured to fit closely to a wearer's body (e.g., a user's torso or a user's upper torso, so as to cover the user's heart and lungs). In various embodiments, the wearable device 40 may comprise a controller 45 (e.g., computing device, one or more computer processors, a wireless communication transceiver and/or the like). FIG. 4 provides an illustrative schematic representative of a wearable device controller 45 that can be used in conjunction with embodiments of the present invention. The wearable device controller 45 may be integrated into the wearable device 40 (e.g., article or garment) and may be in wired or wireless communication with sensors 407, 411A-N, 413A-N of the wearable device 40. In some embodiments, the wearable device controller 45 may be in wireless communication with, but physically distinct from, the wearable device 40 (e.g., via short-range wireless communication, such as Bluetooth, via long-range wireless communication, and/or the like). In some embodiments, the wearable device controller 45 may be configured to receive inputs and/or generate outputs for display via a user interface of the wearable device 40.

The wearable device controller 45 may be configured to obtain (e.g., receive, store, retrieve and/the like) and/or process raw information/data (e.g., audio sensor data, video sensor data and/or the like) obtained from various sensors 407, 411A-N, 413A-N of the wearable device 40 in order to determine one or more values and/or characteristics describing the data that lead to performing predictive tasks. In some embodiments, each sensor 407, 411A-N, 413A-N may be associated with a sensor identifier corresponding with a known location within the wearable device such that the location of each of the sensors 407, 411A-N, 413A-N within the wearable device 40 and relative to each of the other sensors can be determined. Accordingly, sensor data (e.g., audio sensor data) may comprise sensor identifier information/data (e.g., metadata, timestamp data and/or the like). The wearable device controller 45 may be configured to utilize the sensor identifier information/data in order to correlate respective portions (e.g., instances, segments and/or the like) of sensor data (e.g., audio sensor data) with a corresponding known location of a particular sensor of the wearable device 40. In some embodiments, the wearable device controller 45 may be configured to process at least some of the raw information/data (e.g., audio sensor data, video sensor data and/or the like) locally and/or obtain additional data to aid in local processing. For example, the wearable device controller 45 may be configured to locally execute various algorithms on at least a portion of the raw and/or processed information/data obtained by the wearable device controller 45. For example, the wearable device controller 45 may be configured to execute a EVM algorithm on at least a portion of the video sensor data and/or a machine learning model/algorithm on at least a portion of the audio sensor data. In some embodiments, the wearable device controller 45 may be configured to transmit at least a portion of the raw and/or processed information/data for remote processing.

In various embodiments, the wearable device controller 45 may be configured to obtain additional data (e.g., body data) from a user computing entity 20 (e.g., another wearable device, mobile device, computing entity and/or the like) or from the management computing entity 10. The wearable device controller 45 may be configured to generate diagnosis data for the user of the wearable device 40 based at least in part on the determined values and/or characteristics of the raw and/or processed information/data and the obtained body data. The wearable device 40 may transmit at least a portion of the raw and/or processed information/data, the determined values and/or characteristics, and/or the diagnosis data to a management computing entity 10 and/or the user computing entity 20. Additionally and/or alternatively, a user computing entity 20, management computing entity 10 or another remote computing entity may receive and process at least a portion of the raw and/or processed information/data (e.g., audio sensor data and video sensor data). In various embodiments, a user may operate (e.g., control, activate, interact with and/or the like) the wearable device 40 via a mobile application executing on a user computing entity 20. In some embodiments, the wearable device 40 may comprise additional components similar the user computing entity 20.

As shown in FIG. 4, a wearable device controller 45 of certain embodiments includes an antenna 412, a transmitter 404 (e.g., radio), a receiver 406 (e.g., radio), and a processing element 408 that provides signals to and receives signals from the transmitter 404 and receiver 406, respectively. The signals provided to and received from the transmitter 404 and the receiver 406, respectively, may include signaling information/data in accordance with an air interface standard of applicable wireless systems to communicate with various devices, such as a management computing entity 10, user computing entity 20, and/or the like. The wearable device controller 45 may also include one or more network and/or communications interfaces 420 for communicating with various computing entities, such as by communicating data, content, information, and/or similar terms used herein interchangeably that can be transmitted, received, operated on, processed, displayed, stored, and/or the like. In some embodiments, the transmitter 404 and receiver 406 may be embodied as a wireless communication transceiver. In an example embodiment, the transmitter 404 and/or receiver 406 are configured to communicate via one or more SRC protocols. For example, the transmitter 404 and/or receiver 406 may be configured to transmit and/or receive information/data, transmissions, and/or the like of at least one of Bluetooth protocols, low energy Bluetooth protocols, NFC protocols, RFID protocols, IR protocols, Wi-Fi protocols, ZigBee protocols, Z-Wave protocols, 6LoWPAN protocols, and/or other short range communication protocol. In various embodiments, the antenna 412, transmitter 404, and receiver 406 may be configured to communicate via one or more long range protocols, such as GPRS, UMTS, CDMA200, 1×RTT, WCDMA, GSM, EDGE, TD-SCDMA, LTE, E-UTRAN, EVDO, HSPA, HSDPA, Wi-Fi, Wi-Fi Direct, WiMAX, and/or the like.

In this regard, the wearable device controller 45 may be capable of operating with one or more air interface standards, communication protocols, modulation types, and access types. More particularly, the wearable device controller 45 may operate in accordance with any of a number of wireless communication standards and protocols. In a particular embodiment, the wearable device controller 45 may operate in accordance with multiple wireless communication standards and protocols, such as GPRS, UMTS, CDMA200, 1×RTT, WCDMA, TD-SCDMA, LTE, E-UTRAN, EVDO, HSPA, HSDPA, Wi-Fi, WiMAX, UWB, IR protocols, Bluetooth protocols, USB protocols, and/or any other wireless protocol.

Via these communication standards and protocols, the wearable device controller 45 can communicate with various other devices using concepts such as Unstructured Supplementary Service information/data (USSD), Short Message Service (SMS), Multimedia Messaging Service (MMS), Dual-Tone Multi-Frequency Signaling (DTMF), and/or Subscriber Identity Module Dialer (SIM dialer). The wearable device controller 45 can also download changes, add-ons, and updates, for instance, to its firmware, software (e.g., including executable instructions, applications, program modules), and operating system.

In various example embodiments, the user computing entity 20 may comprise one or more sensors 407, 411A-N, 413A-N for receiving or capturing biometric inputs or information/data (e.g., regularly, continuously, or in response to certain triggers). For example, the wearable device 40 may comprise video sensors (e.g., cameras and/or image capturing devices) configured to capture images (e.g., image information/data). In certain embodiments, the wearable device 40 may comprise one or more audio sensors (e.g., microphones) configured to capture audio data. It should be understood that certain wearable devices 40 may comprise combinations of a plurality of sensor types. In some embodiments, the wearable device 40 may comprise microelectromechanical (MEMS) components, biological and chemical sensing components, electrocardiogram (ECG) components, electromyogram (EMG) components, electroencephalogram (EEG)-based neural sensing components, optical sensing components, electrical sensing components, sound components, vibration sensing components and/or the like. Through such components various types of physiological information/data can be captured-such as heart rate information/data, oxygen saturation information/data, carbon dioxide information/data, temperature information/data, breath rate information/data, perspiration information/data, neural information/data, cardiovascular sounds information/data, pulmonary sounds information/data, and/or various other types of information/data.

In addition to a wearable device controller 45, in certain embodiments, the wearable device 40 may comprise a user interface device (not shown) comprising one or more user input/output interfaces (e.g., a button, display and/or speaker/speaker driver coupled to a processing element and/or wearable device controller 45 and a touch interface, keyboard, mouse, and/or microphone coupled to a processing element and/or wearable device controller 45). For example, the user interface may be configured to cause display or audible presentation of information/data and for user interaction therewith via one or more user input interfaces. Moreover, the user interface can comprise or be in communication with any of a number of devices allowing the wearable device controller 45 to receive information/data, such as a keypad (hard or soft), a touch display, voice/speech or motion interfaces, scanners, readers, or other input device. In addition to providing input, the user input interface can be used, for example, to activate or deactivate certain functions, such as screen savers and/or sleep modes. Through such inputs the wearable device controller 45 can capture, collect, store information/data, user interaction/input and/or the like.

The wearable device controller 45 can also include volatile storage or memory 422 and/or non-volatile storage or memory 424, which can be embedded and/or may be removable. For example, the non-volatile memory may be ROM, PROM, EPROM, EEPROM, flash memory, MMCs, SD memory cards, Memory Sticks, CBRAM, PRAM, FeRAM, RRAM, SONOS, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. The volatile and non-volatile storage or memory can store databases, database instances, database management system entities, information/data, applications, programs, program modules, scripts, source code, object code, byte code, compiled code, interpreted code, machine code, executable instructions, and/or the like to implement the functions of the wearable device controller 45.

Exemplary Networks

In one embodiment, any two or more of the illustrative components of the system architecture 100 of FIG. 1 may be configured to communicate with one another via one or more networks 30. The networks 30 may include, but are not limited to, any one or a combination of different types of suitable communications networks such as, for example, cable networks, public networks (e.g., the Internet), private networks (e.g., frame-relay networks), wireless networks, cellular networks, telephone networks (e.g., a public switched telephone network), or any other suitable private and/or public networks. Further, the networks 30 may have any suitable communication range associated therewith and may include, for example, global networks (e.g., the Internet), MANs, WANs, LANs, or PANs. In addition, the networks 30 may include any type of medium over which network traffic may be carried including, but not limited to, coaxial cable, twisted-pair wire, optical fiber, a hybrid fiber coaxial (HFC) medium, microwave terrestrial transceivers, radio frequency communication mediums, satellite communication mediums, or any combination thereof, as well as a variety of network devices and computing platforms provided by network providers or other entities.

Exemplary Wearable Device

As noted above, the wearable device 40 may comprise or be an article or garment configured to fit closely to a wearer's body. The wearable device 40 may comprise, for example and without limitation, a jacket, vest, shirt, pants, shorts, underwear, hat, socks, scarf, neck warmer, leg gaiter, head band, arm band, leg band, a patch, combinations thereof and/or the like.

FIGS. 5A-5B illustrate an example wearable device 40. As shown, the wearable device is a sleeveless vest configured to fit closely to at least a portion of a user's chest/thorax. As shown, the wearable device 40 comprises a front portion 500 configured to be worn adjacent at least a portion of a user's anterior body and a rear portion 510 configured to be worn adjacent at least a portion of the user's posterior body. As further illustrated in FIGS. 5A-5B, the wearable device 40 defines at least a collar portion 501, a body portion 503 and an interior portion 505.

Referring to FIG. 5A, the front portion 500 of the wearable device 40 comprises a collar portion 501 configured to be worn adjacent at least a portion of a user's neck, shoulders and/or similar terms used herein interchangeably. As shown, the collar portion 501 comprises a video sensor 407 positioned close to the right hand side of the user's neck, shoulders and/or the like (when worn by the user). The video sensor 407 can be removably attached to and/or otherwise integrated with the collar portion 501 of the wearable device. In some embodiments, the video sensor 407 may be adjustable and/or include one or more support structures. The video sensor 407 may be or comprise an image capturing apparatus (e.g., camera, wide-angle camera and/or the like) positioned and configured to capture raw image information/data (e.g., video sensor data) within a field of view of the video sensor 407. In some embodiments, image capturing apparatus is oriented such that the field of view encompasses a portion of the interior of the wearable device, such that, when the wearable device is worn by a user, the field of view encompasses an area (e.g., a rectangular area) located on the right hand side of the user's body between the user's right ear or chin and upper chest/thorax.

As shown, the front portion 500 of the wearable device 40 comprises a first plurality of audio sensors 411A-N spaced and attached and/or integrated with the body portion 503 of the wearable device 40. Each of the first plurality of audio sensors 411A-N may be in wired or wireless communication with the wearable device 40. Each of the first plurality of audio sensors 411A-N may be associated with a sensor identifier corresponding with a known location within the wearable device 40 such that the location of each sensor within the wearable device 40 and relative to each of the other sensors can be determined. Additionally, the sensor identifier can facilitate correlation of at least a portion (e.g., instance, segment and/or the like) of sensor data (e.g., audio sensor data, video sensor data and/the like) with a particular sensor. As shown, the first plurality of audio sensors 411A-N is spaced to form a uniform array configured to be worn adjacent at least a portion of an anterior chest/thorax area of the user. An array of audio sensors may be configured to cover an area corresponding with one or more internal organs of the user. As a specific example, the array of audio sensors may be positioned within the wearable device such that, when worn by a user, the array of sensors covers the heart and lungs of the user. The array of audio sensors can be configured in one or more polygonal arrangements (e.g., one or more rectangles, squares, triangles and/or the like) and/or various other arrangements. Additionally, the array of sensors may comprise different types of sensors and/or may be specifically calibrated to obtain data from a particular organ (e.g., an audio sensor configured to obtain heart sounds may be more sensitive than an audio sensor configured to obtain lung sounds). A particular sensor type or calibrated sensor may be located in a portion of the wearable device 40 that corresponds with a general expected location of one or more particular organs when the wearable device 40 is worn. Each of the first plurality of audio sensors 411A-N is configured to capture raw information/data generated by one or more internal organs of the user's body (i.e., captured from within the interior portion 505 of the wearable device 40). As a specific example, an array of sensors located on a chest and back region of a wearable device may be configured to capture sound data regarding the functionality of a wearing user's heart and/or lungs (e.g., capturing heart sounds, capturing breathing sounds, and/or the like). Example methods of identifying audio sounds that may be used in accordance with various embodiments are described in more detail in U.S. patent application Ser. No. 17/096,035, filed Nov. 12, 2020, the contents of which are incorporated herein by reference in their entirety.

FIG. 5B illustrates an example rear portion 510 of the wearable device 40 of FIG. 5A also defining at least the collar portion 501, the body portion 503 and the interior portion 505.

As shown, the rear portion 510 of the wearable device 40 comprises a second plurality of audio sensors 413A-N spaced and attached and/or integrated with the body portion 503 of the wearable device 40. Each of the second plurality of audio sensors 413A-N may be in wired or wireless communication with the wearable device 40. Each of the first plurality of audio sensors 413A-N may be associated with a sensor identifier corresponding with a known location within the wearable device 40 such that the location of each sensor within the wearable device 40 and relative to each of the other sensors can be determined. Additionally, the sensor identifier can facilitate correlation of at least a portion (e.g., instance, segment and/or the like) of sensor data (e.g., audio sensor data, video sensor data and/the like) with a particular sensor. As shown, the second plurality of audio sensors 413A-N is spaced to form a uniform array configured to be worn adjacent at least a portion of an anterior chest/thorax area of the user. An array of audio sensors may be configured to cover an area corresponding with one or more internal organs of the user (e.g., a user's heart and/or a user's lungs) when the wearable device is worn by the user. The array of audio sensors can be configured in one or more polygonal arrangements (e.g., one or more rectangles, squares, triangles and/or the like) and/or various other arrangements. Additionally, the array of sensors may comprise different types of sensors and/or may be specifically calibrated to obtain data from a particular organ (e.g., an audio sensor configured to obtain heart sounds may be more sensitive than an audio sensor configured to obtain lung sounds). A particular sensor type or calibrated sensor may be located in a portion of the wearable device 40 that corresponds with a general expected location of one or more particular organs when the wearable device 40 is worn. Each of the first plurality of audio sensors 413A-N is configured to capture raw information/data generated by one or more internal organs of the user's body (i.e., captured from within the interior portion 505 of the wearable device 40. As a specific example, each of the first plurality of audio sensors 413A-N is configured to capture raw information/data regarding sounds generated by the lungs and/or heart of a wearing user.

V. Exemplary Operation

FIGS. 6, 7A and 7B are example schematics illustrating regions of a body; FIGS. 8, 9, 10, 11 and 12 are flowcharts illustrating example steps, processes, procedures, and/or operations; and FIGS. 13 and 14 are example operational examples/views of user interfaces.

Although the following exemplary operations are described as being performed by one of the wearable device 40, the management computing entity 10 or the user computing entity 20, it should be understood that in various embodiments, the operations can be interchangeably performed by other components within the system architecture 100.

Exemplary Operations of JVP Measurements

Returning to FIG. 4, the wearable device 40 (e.g., the processing element 408 of the wearable device controller 45) is configured to retrieve obtained information/data (e.g., audio sensor data, video sensor data) captured by the sensors 407, 411A-N, 413A-N of the wearable device 40. The wearable device 40 is configured to determine one or more values and characteristics based at least in part on at least a portion of the obtained information/data. In certain embodiments, the wearable device 40 may be configured to determine a Jugular Venous Pressure (JVP) value based at least in part on the video sensor data and determine audio characteristics that lead to generating an audio heat map based at least in part on the audio sensor data.

In various embodiments, the wearable device 40 is configured to determine a JVP value for a user based at least in part on video sensor data for the user. A JVP value that is too high or too low (i.e., above or below a given threshold) may be indicative of increased or decreased blood volume, respectively, and correspond with a serious or emergent condition of the user (e.g., heart failure, constrictive pericarditis, fluid overload, renal disease, superior vena cava obstruction, hypovolemia, and/or the like). The JVP value for a patient corresponds with an indirectly observed pressure for the venous system of a user's body that is usually measured through visualization of pulsations of the internal jugular vein as discussed herein.

FIG. 8 is a flowchart diagram illustrating an example process 800 for determining a JVP value by a wearable device 40.

Beginning at step/operation 802, the wearable device 40 obtains (e.g., receives, retrieves, and/or the like) video sensor data captured by a video sensor 407. The video sensor 407 may be or comprise a camera and/or image capturing device configured to capture images within a field of view. The field of view may be the right hand side of the user's body, between the right ear or chin and the right upper chest/thorax. The field of view may include at least a portion of the location of the external jugular vein and/or internal jugular vein. In some embodiments, the video sensor 407 may be configured to automatically and/or dynamically adjust various settings (e.g., zoom, focus, color, sharpness, brightness and/or the like) in order to facilitate identification of at least a portion of the inferred location of the internal jugular vein and/or the location of the external jugular vein within the field of view of the video sensor 407.

Next, at step/operation 804, the wearable device 40 identifies a region of interest within the field of view captured by video sensor 407. The region of interest may comprise a portion of the field of view corresponding with the location of one or more internal body components such as the user's internal jugular vein, external jugular vein, clavicle, sternocleidomastoid (SCM) muscle and sternal notch baseline. By way of example, the wearable device 40 may utilize a trained machine learning model/algorithm to identify one or more internal body components (e.g., the user's internal jugular vein) within the field of view captured by the video sensor data. The machine learning model/algorithm may be trained on historical video sensor data to identify various visual characteristics and/or attributes. For example, the historical video sensor data may be used to facilitate identification of shapes, outlines and/or movement patterns (e.g., movement patterns of the external jugular vein) and/or any other identifiable visual attributes in the video sensor data. By way of example, the machine learning model/algorithm may be a Convolutional Neural Network (CNN), a Recurrent Neural Network (RNN), and/or the like.

At step/operation 806, the wearable device 40 executes a EVM algorithm on at least a portion of video sensor data to determine a JVP value for the user. The EVM is a spatiotemporal video processing algorithm that processes an input video sequence comprising a plurality of frames (e.g., a plurality of consecutive image frames that collectively define a video) by applying spatial decomposition and temporal filtering in order to reconstruct the plurality of frames. The resulting signal is then amplified to emphasize spatial changes between images/objects within frames, facilitating visualization of otherwise imperceptible/minute changes of motion captured in the frames. The output video sequence of the EVM algorithm reveals features at selected temporal frequencies that are imperceptible in the unprocessed input video sequence. For example, the output of an EVM algorithm executed for an input video sequence depicting a region of interest corresponding with the location of the user's internal jugular vein reveals pulsations of the internal jugular vein that are imperceptible by humans in the unprocessed input video sequence. In certain embodiments, the wearable device 40 may use other algorithms and techniques to determine the JVP value for the user. Additionally and/or alternatively, the wearable device 40 may periodically obtain the user's JVP value (e.g., at certain intervals while the user is wearing the wearable device 40) or determine the JVP value in response to certain triggers (e.g., in response to sternal notch baseline, neck, ear or other body component being within view of the video sensor while the user is wearing the wearable device 40). In some embodiments, the wearable device 40 may store at least a portion of the raw and/or processed video sensor data and provide at least a portion of the raw and/or processed video sensor data to the management computing entity 10 for manual review (e.g., by a clinician). The wearable device 40 may also provide and/or store video identifier data/information (e.g., metadata, timestamp data and/or the like) in association with the raw and/or processed video sensor data and/or the determined JVP value.

As noted above, the wearable device 40 is also configured to determine audio characteristics based at least in part on the audio sensor data and process at least a portion of the audio sensor data (e.g., to generate an audio heat map). The audio characteristics may comprise various attributes such as clarity/quality, pitch, loudness, duration, intensity and timbre.

Exemplary Operations of Audio Heat Map Generation

FIG. 9 is a flowchart diagram illustrating an example process 900 for generating a heat map of audio sensors by the wearable device 40.

Beginning at step/operation 902, the wearable device 40 obtains (e.g., receives, retrieves, and/or the like) audio sensor data captured by one or more audio sensors (e.g., an audio sensor array). The audio sensor data may comprise sensor identifier information/data (e.g., metadata, timestamp data and/or the like). Each of the audio sensors in the audio sensor array may be associated with a sensor identifier corresponding with a known location within the wearable device 40 such that the location of each sensor within the wearable device 40 and relative to each of the other sensors can be determined. Because the location of each sensor is known, sound data generated by a particular sensor may be mapped to a corresponding location within a graphically displayed representation of the wearable device. The sensor identifier information/data may be used to correlate respective portions (e.g., instances, segments and/or the like) of audio sensor data with a corresponding known location of a particular audio sensor in the audio sensor array and within the wearable device 40. The sensor array may be configured to cover an area encompassing a plurality of internal organs in order to facilitate detailed mapping of audio sensors with one or more internal organs and/or organ regions. Accordingly, the approximate location and outline of an organ may be correlated with a subset of audio sensors in the sensor array. In some embodiments, each audio sensor within a sensor array may be generally correlated with one or more regions of an organ. For example, referring to FIGS. 5A-5B, the wearable device 40 may correlate each of the first and second plurality of audio sensors 411A-N, 413A-N with one or more regions corresponding with an internal organ (e.g., a lung region, a heart region and/or the like).

FIG. 6 provides an exemplary schematic 600 illustrating a plurality of heart regions associated with an anterior portion of a body 602. As shown, the plurality of heart regions comprise an aortic heart region 604, a pulmonic heart region 606, an Erb's point heart region 608, a tricuspid heart region 610 and a mitral heart region 612. In some embodiments, the wearable device 40 may associate each of the first plurality of audio sensors 411A-N (not shown) of the wearable device 40 located adjacent the anterior portion of the body 602 with one of the heart regions 604, 606, 608, 610, 612. Then, the wearable device 40 may select a subset of the plurality of audio sensors 411A-N (not shown) that captured high quality audio data (e.g., associated with audio characteristics such as clarity, loudness and/or the like) that are located within a threshold distance of or other associated with the respective heart region 604, 606, 608, 610, 612 for further operations.

FIGS. 7A-B provide example schematics 700, 701 illustrating lung regions associated with an anterior and posterior portion of a body 702, 703, respectively.

Referring to FIG. 7A, the schematic 700 illustrates a plurality of anterior lung regions associated with an anterior portion of a body 702. As shown, the plurality of anterior lung regions comprises an anterior apices lung region 704A-B, an anterior superior lobe lung region 706A-B, an anterior middle lobe lung region 708A-B and an anterior inferior lobe lung region 710A-B. In some embodiments, the wearable device 40 may associate each of the first plurality of audio sensors 411A-N (not shown) of the wearable device located adjacent the anterior portion of the body with one or more of the anterior lung regions 704A-B, 706A-B, 708A-B, 710A-B. Then, the wearable device 40 may select a subset of the first plurality of audio sensors 411A-N (not shown) that captured high quality audio data (e.g., associated with audio characteristics such as clarity, loudness and/or the like) that are located within a threshold distance of or otherwise associated with the respective anterior lung region 704A-B, 706A-B, 708A-B, 710A-B for further operations.

Referring to FIG. 7B, the schematic 701 illustrates a plurality of posterior lung regions associated with a posterior portion of a body 703. As shown, the plurality of posterior lung regions comprise a posterior apices lung region 705A-B, a posterior superior lobe lung region 707A-B, a posterior middle lobe lung region 709A-B and a posterior inferior lobe lung region 711A-B. In some embodiments, the wearable device 40 may associate each of a second plurality of audio sensors 413A-N (not shown) located adjacent the posterior portion of the body with one of the plurality of posterior lung regions 705A-B, 707A-B, 709A-B, 711A-B.

Then, the wearable device 40 may select a subset of the second plurality of audio sensors 413A-N (not shown) that captured high quality audio data (e.g., associated with audio characteristics such as clarity, loudness and/or the like) that are located within a threshold distance of or otherwise associated with the respective posterior lung region 705A-B, 707A-B, 709A-B, 711A-B for further operations.

Returning to FIG. 9, at step/operation 904, the wearable device 40 determines audio characteristics based at least in part on the audio sensor data. In some embodiments, the wearable device 40 may categorize (e.g., rank, score and/or the like) a subset of audio sensors associated with a particular organ and/or an organ region based at least in part on one or more audio characteristics criteria. For example, the wearable device 40 may assign a score and/or rank to each audio sensor based at least in part on corresponding audio sensor data that is the loudest, the clearest and/or the like. The wearable device 40 may correlate one or more sensors to each organ region. For example, by correlating the sensor identifier information/data for each sensor with a known position within the wearable device 40, based at least in part on a relative position to other sensors identified as generally associated with a particular organ and/or based at least in part on machine learning models/algorithms comparing sound signatures from each audio sensor against known sound signatures corresponding with each particular organ region. In various embodiments, a single sensor can be correlated with a single organ region, or more than one sensor can be correlated with a single organ region.

By way of example, the wearable device 40 may select a subset of audio sensors from the first and second plurality of audio sensors 411A-N, 413A-N that capture the highest quality audio data for a corresponding region of an internal organ. For example, the wearable device 40 may select a subset of audio sensors that satisfies one or more threshold quality parameters (e.g., a threshold bitrate, sample rate and/or the like). For example, the wearable device 40 may perform various operations (e.g., apply a Fast Fourier Transform (FFT), filtering operations and/or the like) on portions (e.g., instances, segments and/or the like) of the audio sensor data (e.g., audio signals) corresponding with each of the plurality of audio sensors 411A-N, 413A-N in order to compare characteristic differences (e.g., amplitude, frequency, phase and/or the like) for the audio sensor data (e.g., audio signals) corresponding with each of the audio sensors 411A-N, 413A-N. Then, the wearable device 40 may rank the plurality of audio sensors based at least in part on the determined characteristic differences. For example, an audio signal containing higher frequencies may be indicative of higher quality audio data.

Then, at step/operation 906, the wearable device 40 generates an audio heat map corresponding to at least one internal organ of the wearer (i.e., organ-specific data) based at least in part on the determined audio characteristics. The audio heat map can be a visual representation (e.g., spectrogram, sonograph, voiceprint and/or the like) of the spectrum of frequencies of an audio signal as it varies with time. The audio heatmap may be an image of a wearable device and incorporating different variations of color and/or brightness to visually represent audio sensor data generated by each of the plurality of audio sensors (with particular colors utilized to reflect audio characteristics of sound data generated by each of the plurality of audio sensors, with the corresponding colors mapped to particular locations of the visually displayed wearable device such that the generated heat map reflects sounds detected at each location of a corresponding sensor. In some embodiments, the wearable device 40 may generate an audio heat map for a given organ (e.g., a lung) by selecting one or more audio sensors from the subset of audio sensors that are associated with an organ region and discarding the audio sensor data associated with unselected audio sensors for the organ region. Accordingly, an audio heat map/visual representation for an organ defining a general outline and/or particular regions of the organ can be generated. As described above, with respect to identifying a region of interest, the wearable device 40 may use similar machine learning models/algorithms perform predictive tasks in relation to an audio heat map. The machine learning model/algorithm may be trained on available historical audio heat maps. The machine learning model/algorithm may be a Convolutional Neural Network (CNN), a Recurrent Neural Network (RNN), and/or the like.

Wearable Device Setup and Clinical Procedure Processes

A user may obtain a wearable device 40 (e.g., from a clinician) for remote monitoring of characteristics of the user's body (e.g., heart function, lung function, and/or the like). The user may interact with the wearable device 40 using a mobile application executing on a user computing entity 20. In some embodiments, the user may interact directly with the wearable device 40 (e.g., via a user interface or input device of the wearable device 40).

FIG. 10 is a flowchart diagram illustrating an example setup process 1000 for a wearable device 40.

Beginning at step/operation 1002, a variety of sources can provide (e.g., transmit, send) a mobile application for download and execution on a user computing entity 20 (e.g., in response to a request to download the mobile application generated at the user computing entity 20). In another embodiment, the mobile application may be pre-installed on the user computing entity 20. And in yet another embodiment, the mobile application may be a browser executing on the user computing entity 20. The mobile application may comprise computer-executable program code (e.g., a software application) that provides the functionality described herein. The mobile application may be executed as illustrated at step/operation 1002 to enable various functionalities as discussed herein. Moreover, although specifically referenced as a mobile application, it should be understood that the mobile application may be executable by any of a variety of computing entity types, such as desktop computers, laptop computers, mobile devices, and/or the like.

In some embodiments, step/operation 1002 is performed as part of registering a user. For example, a user profile for a user may be generated/created as part of registration. However, as will be recognized, a user profile may already exist and be stored in a user profile database; in such a case, registration may simply link to an existing user profile. Each user profile may be identifiable via one or more identifiers (e.g., social security numbers, patient IDs, member IDs, participant IDs, usernames, globally unique identifiers (GUIDs), universally unique identifiers (UUIDs), and/or the like) configured to uniquely identify the user profile. Thus, as part of enrolling/registering a user, the mobile application (executing on the user computing entity 20) may request and receive various types of information/data. For example, the mobile application (executing on the user computing entity 20) may request a user identifier or username. If a user profile corresponding to the user and associated with a user identifier already exists (e.g., is stored in a user profile database), the user information/data may comprise the user's access credentials (e.g., username, password, and/or the like). If a user profile corresponding to the user does not already exist, the user information/data may comprise information/data identifying the user (e.g., a username, a birthdate, and/or the like), user contact information/data (e.g., an electronic destination address, an email address, an instant messenger username, a social media username, an app username, a phone number associated with the user computing entity 20, a mailing address, and/or the like), electronic medical record (EMR) number, and/or other information/data relevant to the application (e.g., user account number, user affiliation, user title or role, and/or the like). In various embodiments, the mobile application (executing on the user computing entity 20) receives the user information/data (e.g., via one or more user interfaces) and can provide the same to the management computing entity 10 for the generation/creation of and/or storage with a user profile. A user's EMR may be associated with and/or otherwise stored in conjunction with the user profile. In some embodiments, the user may initiate synchronization of the wearable device 40 with the EMR and/or user profile stored by the management computing entity 10 in order to ensure privacy and proper identification of the device before each use.

At step/operation 1004, the user receives instructions via a user interface of the mobile application executing on the user computing entity 20, to wear the wearable device 40 for a prescribed duration. In various embodiments, the instructions may be automatically generated (e.g., by the management computing entity 10) or provided based at least in part in response to clinician input/instructions provided by a clinician interacting with the management computing entity 10. In some embodiments, instructions may be provided automatically subsequent to an in-person physician appointment or a virtual appointment. The instructions may comprise messages in the form of banners, headers, notifications, and/or the like. The instructions may include one or more target times and/or other target parameters (e.g., after eating, after exercising, at a particular time of day, before or after taking medication and/or the like) for wearing the wearable device 40. Additionally and/or alternatively, the instructions may be provided via a user interface of the wearable device 40, email, text message, automated phone calls and/or the like. By way of example, the user may receive the following message via the user interface of the mobile application: "John, please wear the device for an hour in the morning and an hour in the evening after taking your prescribed medication."

Next, at step/operation 1006, the user may initiate data collection by the sensors 407, 411A-N, 413A-N of the wearable device 40. For example, the user may provide input via the mobile application executing on the user computing entity 20 or may provide input via an input device and/or user interface of the wearable device 40. In some embodiments, at least a portion of the obtained wearable device sensor data (e.g., audio sensor data and video sensor data) may be transferred to the user computing entity 20 and/or the management computing entity 10 for performing at least a portion of the required operations (e.g., correlating audio sensor data with organ regions, executing an EVM algorithm and/or the like).

At step/operation 1008 by interacting with a user interface of the mobile application, the user initiates a transfer of the wearable device sensor data and/or body data to an electronic medical record (EMR) and/or user profile stored by the management computing entity 10. In some embodiments, the wearable device 40 may transfer at least a portion of the wearable device sensor data to the user computing entity 20 and/or the management computing entity 10. In some embodiments, the wearable device 40 may be configured to automatically and/or periodically (e.g., at scheduled times) transfer at least a portion of the raw and/or processed information/data utilized by the wearable device 40 (e.g., wearable device sensor data, diagnosis data and/or the like). In other embodiments, the wearable device 40 or user computing entity 20 may be configured to provide information/data in response to requests/queries received from the management computing entity 10. In various embodiments, the wearable device 40 may be managed, calibrated and/or otherwise controlled at least in part by a management computing entity 10.

FIG. 11 is a flowchart diagram illustrating an example clinical procedure process 1100 by a management computing entity 10.

Beginning at step/operation 1102, the management computing entity 10 calibrates the wearable device 40. The management computing entity 10 may associate the wearable device 40 with a stored user profile and an EMR associated with and/or otherwise stored in conjunction with the user profile. The management computing entity 10 may verify that the stored user profile and EMR identifies that the wearable device 40 is associated with the current user. In various embodiments, the management computing entity 10 may modify (e.g., reset, reconfigure and/or the like) wearable device settings before each use or only upon reassignment to a new user. At step/operation 1104, the management computing entity 10 obtains (e.g., receives, requests and/or the like) at least a portion of the raw audio sensor data and/or processed audio sensor data from the wearable device 40. In some embodiments, the raw and/or processed audio sensor data may be provided by the user computing entity 20.

At step/operation 1106, the management computing entity 10 obtains (e.g., receives, requests, and/or the like) raw video sensor data and/or processed video sensor data from the wearable device 40. In some embodiments, the raw and/or processed video sensor data may be provided by the user computing entity 20.

At step/operation 1108, the management computing entity 10 obtains (e.g., receives, requests, and/or the like) raw and/or processed body data and/or additional data from the user computing entity 20 and/or one or more other computing devices. The computing devices may comprise, for example without limitation, health monitoring devices, fitness trackers, watches, wearable patches, wearable textiles and/or the like which are configured to obtain (e.g., monitor, detect, and/or the like) body data. The body data may be or comprise physiological information/data, biometric information/data, accelerometer information/data, location information/data, time information/data and/or the like. In certain embodiments, the body data may include heart rate data, oxygen saturation data, pulse rate data, body temperature data, breath rate data, perspiration data, blink rate data, blood pressure data, neural activity data, cardiovascular data, pulmonary data, and/or various other types of information/data. In some embodiments, the body data may comprise environmental data corresponding with a location of the user such as air quality and air temperature data, allergen data, pollen count, weather information/data, water contamination data and/or the like.

It should be understood that while described separately, in some embodiments, steps/operations 1104, 1106, 1108 may be performed in a different order or combination (e.g., as a single step/operation in which the audio sensor data, video sensor data and other data/information is provided simultaneously).

At step/operation 1110, the management computing entity 10 uses one or more machine learning models/algorithms to process the audio sensor data. The machine learning model/algorithm may comprise computer-implemented operations and/or parameters which are configured to perform predictive tasks. The machine learning model/algorithm may be configured to identify sounds and categorize the sounds using appropriate medical labels. In some embodiments, the management computing entity 10 may be trained classify/ categorize an audio heat map comprising organ-specific data. The machine learning model/algorithm may be trained on historical data from stored audio data. The machine learning model/algorithm may be a neural network, a convolutional neural network, and/or the like. By way of example, the management computing entity 10, using one or more machine learning models/algorithms may process heart or lung sounds and label/categorize the heart or lung sounds as "normal" or "abnormal." An abnormal lung sound may be assigned a label and corresponding label metadata. Label metadata for abnormal lung sounds may include data describing the recorded sounds such as "fine crackles in posterior lung bases" or "coarse wheezes in right lower and middle lungs, left lower long rub." Label metadata for abnormal heart sounds may include data describing the recorded sounds such as "loud P2 in $2^{nd}$ intercostal space," "S3 in left lower sternal border" or "holosystolic mitral regurgitation murmur at apex." The management computing entity 10 may associate the label and corresponding label metadata with a user profile. In some embodiments, the management computing entity 10 may generate user interface data corresponding with at least a portion of the label data and corresponding label metadata.

In various embodiments, the management computing entity 10 or wearable device 40 may proceed to generate diagnosis data for the user. FIG. 12 is a flowchart diagram 1200 illustrating an example process for generating diagnosis data by a management computing entity 10. In some embodiments, diagnosis data may be generated by the wearable device 40 or the user computing entity 20.

In some embodiments, upon determining a JVP value and organ-specific data for a user, at step/operation 1202, the management computing entity 10 obtains (e.g., retrieves, receives, requests and/or the like) body data for the user. Alternatively, the management computing entity 10 may obtain the JVP value, organ-specific data, the body data simultaneously (e.g., from the user computing entity 20).

Next, at step/operation 1204, the management computing entity 10 stores at least a portion of the body data in a temporal relationship with the determined JVP value and organ-specific data for the user. The temporal relationship may be a direct/explicit or implicit relationship indicating causation or correlation between different sources of data. In certain embodiments, a temporal relationship may be established based at least in part on time stamps associated with collected data, thereby providing an order of data collection. Thus, as data is collected from a plurality of audio sensors, data collected simultaneously (or substantially simultaneously) as indicated by the associated time stamps, may be indicated as temporally related in certain embodiments, one or more time-based user interfaces may be generated, such that data generated simultaneously or substantially simultaneously may be displayed within a display corresponding with the particular time. By way of example, the management computing entity 10 may identify a time period and an event and/or user condition corresponding with each of the body data, the JVP value and the organ-specific data. For instance, the management computing entity may identify the following features: from body data, the user's heart rate is elevated above a threshold, from organ-specific data, abnormal lung sound and from processed video sensor data that the user's JVP is above a normal threshold. As mentioned, these determinations may be provided together with corresponding time stamps, so as to determine whether these determinations occur for raw data collected at least substantially simultaneously. The management computing entity 10 may determine that each of the features were captured between a particular time period (e.g., between 12:00 pm and 1:00 pm on the same day). Accordingly, the management computing entity 10 may associate and store the features, the associated time period and a corresponding user condition (e.g., in a data object, table, and/or the like).

Then, at step/operation 1206, the management computing entity 10 processes the stored body data, the JVP value and the organ-specific data in order to generate diagnosis data. In certain embodiments, the wearable device 40 may be configured to generate the diagnosis data instead of the management computing entity 10. The diagnosis data may comprise a prediction in relation to the user's condition such as "stable", "caution", or "emergent. By way of example, the management computing entity 10 the prediction may be based at least in part on body data, a JVP value and organ-specific data that satisfies certain parameters/conditions. The management computing entity 10 may use a machine learning model/algorithm trained on historical diagnosis data in order to generate the diagnosis data. The management computing entity 10 may store/associate the diagnosis data with the corresponding user profile.

The management computing entity 10 may determine the one or more actions to take in relation to the user based at least in part on the diagnosis data. In some embodiments, where the diagnosis data is generated by the wearable device 40 or user computing entity 20, the wearable device 40 or user computing entity 20 may determine the one or more actions to take.

The management computing entity 10 may automatically determine the one or more actions to take based at least in part on stored set definitions/parameters (e.g., if JVP value, stored body data and organ specific data satisfies certain parameters). The diagnosis data and/or determined actions to take may be automatically determined by the management computing entity 10 based at least in part on machine learning models/algorithms, set definitions/stored criteria and/or the like. The management computing entity 10 may generate user interface data based at least in part on at least a portion of the JVP value, body data, organ-specific data and diagnosis data and provide (e.g., transmit, send) the user interface data to one or more client computing entities. In some embodiments, the diagnosis data and/or determined actions may be manually determined by an operator (e.g., clinician) inputting or selecting an action to take based at least in part on a manual review of the user interface data. In some embodiments, the set definitions and/or parameters may be customized for individual users by a clinician.

FIG. 13 provides an operational example of user interface data provided for presentation via a user interface 1300 of a user computing entity 20. As shown, the user interface data comprises a plurality of entries each comprising a user identifier 1302 (e.g., member ID), body data 1304, organ-specific data 1306, a JVP value 1308, diagnosis data 1310 and an action to be taken 1312.

FIG. 14 provides an operational example of determining and/or causing an action to be taken. The wearable device 40/management computing entity 10 may generate an alert or notification based at least in part on a corresponding manually/automatically determined action to be taken.

The wearable device 40/management computing entity 10 may provide one or more data objects corresponding with the alert/notification for presentation by a user computing entity 20 (e.g., for dynamically updating a user interface 1402 of a user computing entity 20). As will be recognized, a variety of other approaches and techniques can be used to adapt to various needs and circumstances.

VI. Conclusion

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only, and not for purposes of limitation.

The invention claimed is:

1. A wearable device configured to be worn by a user, the wearable device comprising:
    a body portion;
    a video sensor configured to capture video data within a field of view of the video sensor;
    a plurality of audio sensors configured to capture audio data; and
    a controller configured to:
        determine a Jugular Venous Pressure (JVP) of the user based at least in part on the video data captured by the video sensor;
        determine a JVP value corresponding to the JVP of the user; and
        determine characteristics of the audio data captured by the plurality of audio sensors to generate an audio heat map corresponding to an internal organ of the user.

2. The wearable device of claim 1, wherein the controller is further configured to execute a Eulerian Video Magnification (EVM) algorithm to determine the JVP of the user based at least in part on the video data.

3. The wearable device of claim 1, wherein the plurality of audio sensors is configured to detect the user's lung, and wherein generating the audio heat map corresponding to the user's lung comprises identifying breathing sounds captured by at least one of the plurality of audio sensors.

4. The wearable device of claim 1, wherein the controller is attached to the wearable device.

5. The wearable device of claim 1, wherein the controller comprises a wireless communication transceiver.

6. The wearable device of claim 1, wherein the body portion of the wearable device defines a front portion and a rear portion, and wherein the plurality of audio sensors comprises a first plurality of audio sensors attached at the front portion of the body portion and a second plurality of audio sensors attached at the rear portion of the body portion.

7. The wearable device of claim 1, wherein the controller is further configured to:
    receive body data obtained from one or more additional sensors associated with the user; and
    store (a) the body data in a temporal relationship with the JVP value and (b) organ-specific data of the user in a non-transitory memory storage area.

8. The wearable device of claim 7, wherein the controller is additionally configured to generate diagnosis data associated with the user based at least in part the body data, the JVP value, and the organ-specific data.

9. The wearable device of claim 1, wherein determining characteristics of the audio data is based at least in part on one or more machine learning models.

10. A computer-implemented method comprising:
    receiving, by one or more processors, video data captured by a video sensor of a wearable device configured to be worn by a user, wherein the video sensor is configured to capture video data within a field of view of the video sensor;
    receiving, by the one or more processors, audio data captured by a plurality of audio sensors of the wearable device;
    determining, by the one or more processors, a Jugular Venous Pressure (JVP) value of the user based at least in part on the video data;
    determining, by the one or more processors, characteristics of the audio data to generate an audio heat map corresponding to an internal organ of the user;
    identifying, by the one or more processors, at least one of the plurality of audio sensors configured to collect organ-specific data of the user; and
    storing, by the one or more processors, the JVP value and the organ-specific data of the user.

11. The computer-implemented method of claim 10, wherein determining the JVP value of the user further comprises:
    executing, by the one or more processors, a Eulerian Video Magnification (EVM) algorithm on the video data.

12. The computer-implemented method of claim 10, wherein the plurality of audio sensors is configured to detect the user's lung, and wherein generating the audio heat map corresponding to the user's lung comprises identifying breathing sounds captured by at least one of the plurality of audio sensors.

13. The computer-implemented method of claim 10, further comprising:
    receiving, by the one or more processors, body data obtained from one or more additional sensors associated with the user; and
    storing, by the one or more processors, (a) the body data in a temporal relationship with the JVP value and (b) organ-specific data of the user in a non-transitory memory storage area.

14. The computer-implemented method of claim 13, further comprising:
    generating, by the one or more processors, diagnosis data associated with the user based at least in part the body data, the JVP value, and the organ-specific data.

15. The computer-implemented method of claim 10, wherein identifying, by the one or more processors, at least one of the plurality of audio sensors configured to collect the organ-specific data of the user is based at least in part on one or more machine learning models.

16. A computer program product comprising at least one non-transitory computer-readable storage medium having computer-readable program code portions stored therein, the computer-readable program code portions configured to:
    receive video data captured by a video sensor of a wearable device configured to be worn by a user, wherein the video sensor is configured to capture video data within a field of view of the video sensor;
    receive audio data captured by a plurality of audio sensors of the wearable device;
    determine a Jugular Venous Pressure (JVP) value of the user based at least in part on the video data;

determine characteristics of the audio data to generate an audio heat map corresponding to an internal organ of the user;

identify at least one of the plurality of audio sensors configured to collect organ-specific data of the user; and store the JVP value and the organ-specific data of the user.

17. The computer program product of claim 16, wherein the computer-readable program code portions are further configured to determine the JVP of the user by at least executing a Eulerian Video Magnification (EVM) algorithm with the video data.

18. The computer program product of claim 16, wherein the computer-readable program code portions are further configured to:

receive body data obtained from one or more additional sensors associated with the user; and store (a) the body data in a temporal relationship with the JVP value and (b) organ-specific data of the user in a non-transitory memory storage area.

19. The computer program product of claim 16, wherein the plurality of audio sensors is configured to detect the user's lung, and wherein generating the audio heat map corresponding to the user's lung comprises identifying breathing sounds captured by at least one of the plurality of audio sensors.

20. The computer program product of claim 18, wherein the computer-readable program code portions are further configured to:

generate diagnosis data associated with the user based at least in part the body data, the JVP value, and the organ-specific data.

* * * * *